(12) United States Patent
Viola et al.

(10) Patent No.: US 6,436,054 B1
(45) Date of Patent: Aug. 20, 2002

(54) BIOPSY SYSTEM

(75) Inventors: Frank Viola, Sandy Hook; Csaba L. Rethy, Fairfield; David Ivanko, Bridgeport; Scott Martinelli, Danbury; Bruce Jankowski, Meriden; Randolph Lehn, Stratford, all of CT (US); James Dale, Nashua; Arthur Stickney, Deering, both of NH (US); Karl Ehrenfels, Ridgefield, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/448,238

(22) Filed: Nov. 24, 1999

Related U.S. Application Data

(60) Provisional application No. 60/109,989, filed on Nov. 25, 1998, and provisional application No. 60/158,667, filed on Oct. 8, 1999.

(51) Int. Cl.$^7$ ............................................... A61B 10/00
(52) U.S. Cl. ....................................................... 600/562
(58) Field of Search .............................. 600/564, 565, 600/658, 571

(56) References Cited

U.S. PATENT DOCUMENTS

| 737,293 | A | 8/1903 | Summerfeldt |
| 1,568,008 | A | 12/1925 | Thomas |
| 1,585,934 | A | 5/1926 | Muir |

(List continued on next page.)

FOREIGN PATENT DOCUMENTS

| CH | 534505 | 6/1970 |
| DE | 935 625 | 11/1955 |
| DE | 1 817 555 | 1/1971 |

(List continued on next page.)

OTHER PUBLICATIONS

Stereotaxic Needle Core Biopsy of Breast Lesions Using a Regular Mammographic Table with an Adaptable Stereotaxic Device, Caines et al., pp. 317–321, Aug. 1993.

(List continued on next page.)

*Primary Examiner*—Kevin Shaver
*Assistant Examiner*—Pamela Wingood

(57) ABSTRACT

A biopsy system is provided including a housing and a biopsy instrument operatively associated with the housing and configured and dimensioned to remove a tissue sample from a patient. A firing module is included that is detachably engageable with the housing and operatively associated with the biopsy instrument to facilitate selective rapid advancement of at least a portion of the biopsy instrument toward a targeted location with the patient. The biopsy instrument includes a tissue receiving portion. The system may include an indexing assembly disposed within the housing and configured to cooperate with the biopsy instrument to selectively orient the tissue receiving portion. The indexing assembly may include a manual gearing assembly configured for selective orientation of the tissue receiving portion. The system may include a linear advancement control assembly disposed within the housing and configured to effect linear actuation of a tubular knife member. An optical sensor may be disposed adjacent a portion of the tubular knife member and oriented to detect the orientation of a lateral opening formed through the tubular knife member. A carriage may be slidably disposed within the housing and configured to releasably retain at least a portion of the biopsy instrument. A method of performing a surgical biopsy is disclosed.

20 Claims, 31 Drawing Sheets

U.S. PATENT DOCUMENTS

| | | |
|---|---|---|
| 1,609,456 A | 12/1926 | Boyle |
| 1,663,761 A | 3/1928 | Johnson |
| 1,867,624 A | 7/1932 | Hoffman |
| 2,117,278 A | 5/1938 | Ainsworth |
| 2,541,542 A | 2/1951 | Perez et al. |
| 2,729,210 A | 1/1956 | Spencer |
| 3,173,414 A | 3/1965 | Guillant |
| 3,400,708 A | 9/1968 | Scheidt |
| 3,470,867 A | 10/1969 | Goldsmith |
| 3,477,423 A | 11/1969 | Griffith |
| 3,561,429 A | 2/1971 | Jewett et al. |
| 3,590,808 A | 7/1971 | Muller |
| 3,605,721 A | 9/1971 | Hallac |
| 3,606,878 A | 9/1971 | Kellogg, Jr. |
| 3,628,524 A | 12/1971 | Jamshidi |
| 3,732,858 A | 5/1973 | Banko |
| 3,734,099 A | 5/1973 | Bender et al. |
| 3,844,272 A | 10/1974 | Banko |
| 3,929,123 A | 12/1975 | Jamshidi |
| 3,989,033 A | 11/1976 | Halpern |
| 3,995,619 A | 12/1976 | Glatzer |
| 4,099,518 A | 7/1978 | Baylis et al. |
| 4,174,715 A | 11/1979 | Hasson |
| 4,177,797 A | 12/1979 | Baylis et al. |
| 4,200,106 A | 4/1980 | Douvas et al. |
| 4,203,444 A | 5/1980 | Bonnell et al. |
| 4,210,146 A | 7/1980 | Banko |
| 4,306,570 A | 12/1981 | Matthews |
| 4,340,066 A | 7/1982 | Shah |
| 4,396,021 A | 8/1983 | Baumgartner |
| 4,445,517 A | 5/1984 | Feild |
| 4,600,014 A | 7/1986 | Beraha |
| 4,644,951 A | 2/1987 | Bays |
| 4,651,753 A | 3/1987 | Lifton |
| 4,660,267 A | 4/1987 | Wheeler |
| 4,662,869 A | 5/1987 | Wright |
| 4,669,473 A | 6/1987 | Richards et al. |
| 4,674,502 A | 6/1987 | Imonti |
| 4,678,459 A | 7/1987 | Onik et al. |
| 4,681,123 A | 7/1987 | Valtchev |
| 4,699,154 A | 10/1987 | Lindgren |
| 4,702,260 A | 10/1987 | Wang |
| 4,702,261 A | 10/1987 | Cornell et al. |
| 4,708,147 A | 11/1987 | Haaga |
| 4,711,250 A | 12/1987 | Gilbaugh, Jr. et al. |
| 4,907,599 A | 3/1990 | Taylor |
| 4,917,100 A | 4/1990 | Nottke |
| 4,924,878 A | 5/1990 | Nottke |
| 4,926,877 A | 5/1990 | Bookwalter |
| 4,931,059 A | 6/1990 | Markham |
| 4,936,835 A | 6/1990 | Haaga |
| RE33,258 E | 7/1990 | Onik et al. |
| 4,940,061 A | 7/1990 | Terwilliger et al. |
| 4,944,308 A | 7/1990 | Akerfeldt |
| 4,953,558 A | 9/1990 | Akerfeldt |
| 4,958,625 A | 9/1990 | Bates et al. |
| 4,971,067 A | 11/1990 | Bolduic et al. |
| 4,976,269 A | 12/1990 | Mehl |
| 4,989,614 A | 2/1991 | Dejter, Jr. et al. |
| 4,991,592 A | 2/1991 | Christ |
| 5,021,059 A | 6/1991 | Kensey et al. |
| 5,031,634 A | 7/1991 | Simon |
| 5,036,860 A | 8/1991 | Leigh et al. |
| 5,047,008 A | 9/1991 | de Juan, Jr. et al. |
| 5,048,538 A | 9/1991 | Terwilliger |
| 5,080,655 A | 1/1992 | Haaga |
| 5,106,364 A | 4/1992 | Hayafuji et al. |
| 5,111,828 A | 5/1992 | Kornberg et al. |
| 5,121,751 A | 6/1992 | Panalletta |
| 5,127,419 A | 7/1992 | Kaldany |
| 5,133,359 A * | 7/1992 | Kedem ........................ 600/568 |
| 5,133,360 A | 7/1992 | Spears |
| RE34,056 E | 9/1992 | Lindgren et al. |
| 5,146,921 A | 9/1992 | Terwilliger et al. |
| 5,148,813 A | 9/1992 | Bucalo |
| 5,183,052 A | 2/1993 | Terwilliger et al. |
| 5,183,054 A | 2/1993 | Burkholder et al. |
| 5,188,118 A | 2/1993 | Terwilliger |
| 5,195,533 A | 3/1993 | Chin et al. |
| 5,195,988 A | 3/1993 | Haaga |
| 5,197,484 A | 3/1993 | Kornberg et al. |
| 5,199,441 A | 4/1993 | Hogle |
| 5,213,110 A | 5/1993 | Kedem et al. |
| 5,217,435 A | 6/1993 | Kring |
| 5,220,926 A | 6/1993 | Jones |
| 5,224,488 A | 7/1993 | Neuffer |
| 5,226,909 A | 7/1993 | Evans et al. |
| 5,226,910 A | 7/1993 | Kayiyama et al. |
| 5,234,994 A | 8/1993 | Shiraki et al. |
| 5,240,011 A * | 8/1993 | Assa .......................... 600/564 |
| 5,249,582 A | 10/1993 | Taylor |
| 5,249,583 A | 10/1993 | Mallaby |
| 5,251,641 A | 10/1993 | Xavier |
| 5,254,105 A | 10/1993 | Haaga |
| 5,257,632 A | 11/1993 | Turkel et al. |
| 5,269,809 A | 12/1993 | Hayhurst et al. |
| 5,271,414 A | 12/1993 | Partika et al. |
| 5,273,051 A | 12/1993 | Wilk |
| 5,282,476 A | 2/1994 | Terwilliger |
| 5,284,156 A | 2/1994 | Schramm et al. |
| 5,285,795 A | 2/1994 | Ryan et al. |
| 5,289,520 A | 2/1994 | Pellegrino et al. |
| 5,290,294 A | 3/1994 | Cox et al. |
| 5,290,303 A | 3/1994 | Pingleton et al. |
| 5,301,684 A | 4/1994 | Ogirala |
| 5,313,958 A | 5/1994 | Bauer |
| 5,316,013 A | 5/1994 | Striebel, II et al. |
| 5,320,110 A | 6/1994 | Wang |
| 5,353,804 A | 10/1994 | Kornberg et al. |
| 5,368,045 A | 11/1994 | Clement et al. |
| 5,405,321 A | 4/1995 | Reeves |
| 5,409,004 A | 4/1995 | Sloan |
| 5,415,169 A | 5/1995 | Siczik et al. |
| 5,415,182 A | 5/1995 | Chin et al. |
| 5,425,376 A | 6/1995 | Banys et al. |
| 5,458,112 A | 10/1995 | Weaver |
| 5,462,062 A | 10/1995 | Rubinstein et al. |
| 5,476,101 A | 12/1995 | Schramm et al. |
| 5,477,862 A | 12/1995 | Haaga |
| 5,488,958 A | 2/1996 | Topel et al. |
| 5,492,130 A | 2/1996 | Chiou |
| 5,505,211 A | 4/1996 | Ohto et al. |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,560,373 A | 10/1996 | De Santis |
| 5,570,699 A | 11/1996 | Kaas |
| 5,649,547 A | 7/1997 | Richart et al. |
| 5,655,542 A | 8/1997 | Weilandt |
| 5,687,739 A | 11/1997 | McPherson et al. |
| 5,752,923 A | 5/1998 | Terwilliger |
| 5,769,086 A | 6/1998 | Ritchart et al. |
| 5,775,333 A | 7/1998 | Burbank et al. |
| 5,779,647 A | 7/1998 | Chau et al. |
| 5,817,033 A | 10/1998 | DeSantis et al. |
| 5,964,716 A * | 10/1999 | Gregoire et al. ............ 600/564 |
| 5,980,469 A * | 11/1999 | Burbank et al. ............ 600/567 |
| 6,120,462 A * | 9/2000 | Hibner ........................ 600/566 |

FOREIGN PATENT DOCUMENTS

| | | |
|---|---|---|
| DE | 27 19 959 A1 | 11/1978 |
| DE | 2919009 | 11/1979 |
| DE | 159 394 | 3/1983 |
| DE | 88 02 580.2 | 9/1988 |
| DE | 42 16 694 A1 | 12/1992 |
| EP | 0 010 321 A1 | 4/1980 |
| EP | 0 019 104 | 11/1980 |
| EP | 0 207 726 A2 | 1/1987 |
| EP | 0 238 461 A1 | 9/1987 |
| EP | 0 378 692 | 7/1990 |
| EP | 0 442 851 A1 | 8/1991 |
| EP | 0 536 888 a1 | 4/1993 |
| EP | 0 561 732 A1 | 9/1993 |
| FR | 1 161 400 | 8/1958 |
| FR | 1 267 960 | 6/1960 |
| FR | 2 332 743 | 6/1977 |
| FR | 2610508 | 10/1987 |
| FR | 2 654 609 | 5/1991 |
| GB | 1 255 330 | 12/1971 |
| GB | 2 237 992 A | 5/1991 |
| SI | 0728 852 | 5/1980 |
| SU | 400319 | 2/1974 |
| SU | 520 976 | 7/1976 |
| SU | 648 219 | 2/1979 |
| SU | 707 576 | 1/1980 |
| SU | 1178 422 A | 9/1985 |
| SU | 1192 795 A | 11/1985 |
| WO | WO 91/01112 | 2/1991 |
| WO | WO 92/00040 | 1/1992 |
| WO | WO 92/19159 | 11/1992 |
| WO | WO 9309720 | 11/1992 |
| WO | WO 93/12707 | 7/1993 |
| WO | WO 83/03343 | 10/1993 |
| WO | WO 93/20753 | 10/1993 |
| WO | WO 94/08512 | 4/1994 |
| WO | WO 88/07839 | 10/1998 |

OTHER PUBLICATIONS

Breast Biopsy: A Comparative Study of Stereotaxially Guided Core and Excisional Techniques, Gisvold et al., pp. 815–820, Apr., 1994.

Stereotactic Core Needle Biopsy of Mammographic Breast Lesions as a Viable Alternative to Surgical Biopsy, Mikhail, MD et al., pp. 363–367, 1994.

Ismet Hallac, M.D., "A New Design in Biopsy Needles", May 10, 1961, pp. 515–517.

Acufex Microsurgical, Inc. Product Brochure, 1994.

* cited by examiner

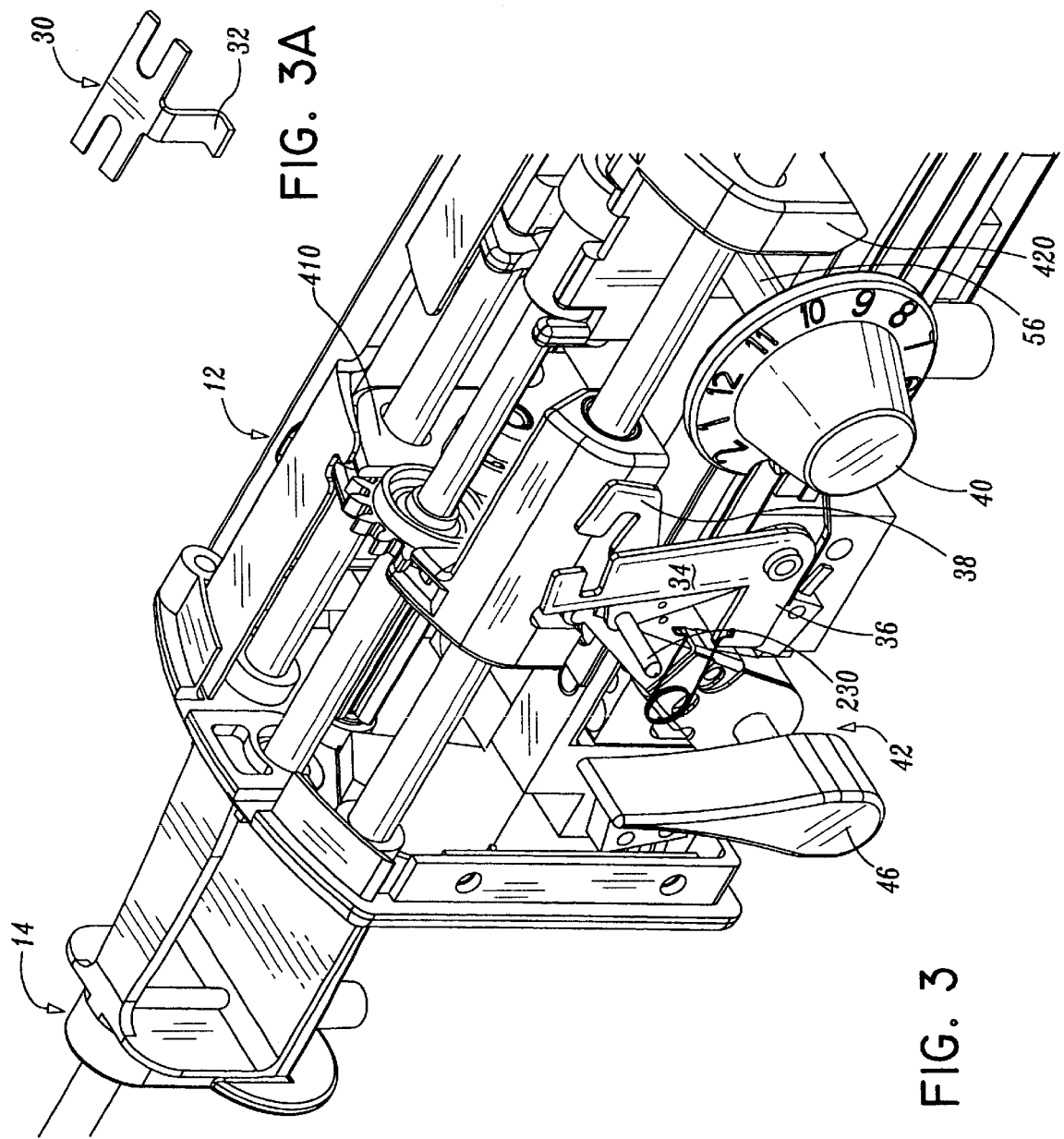

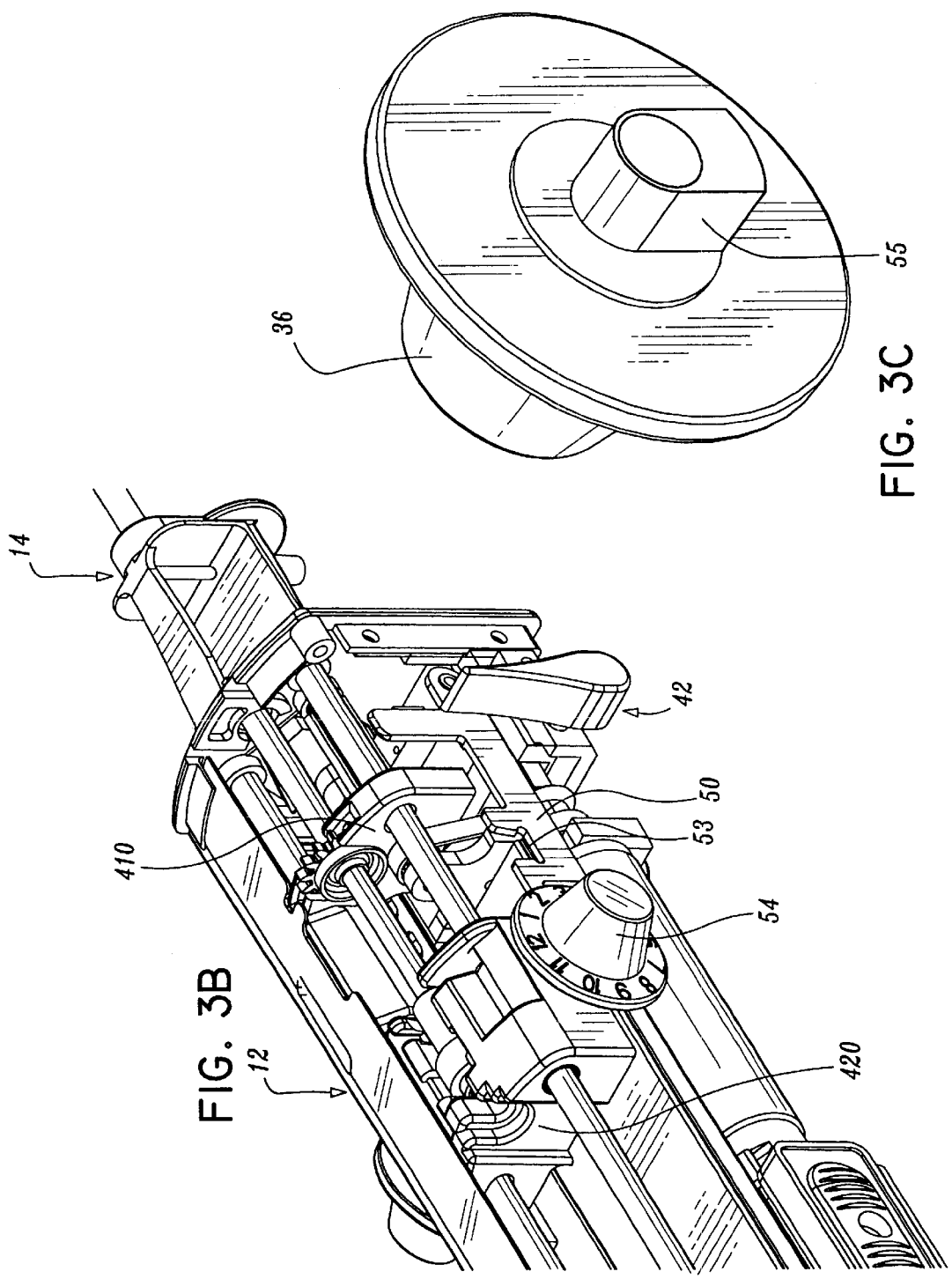

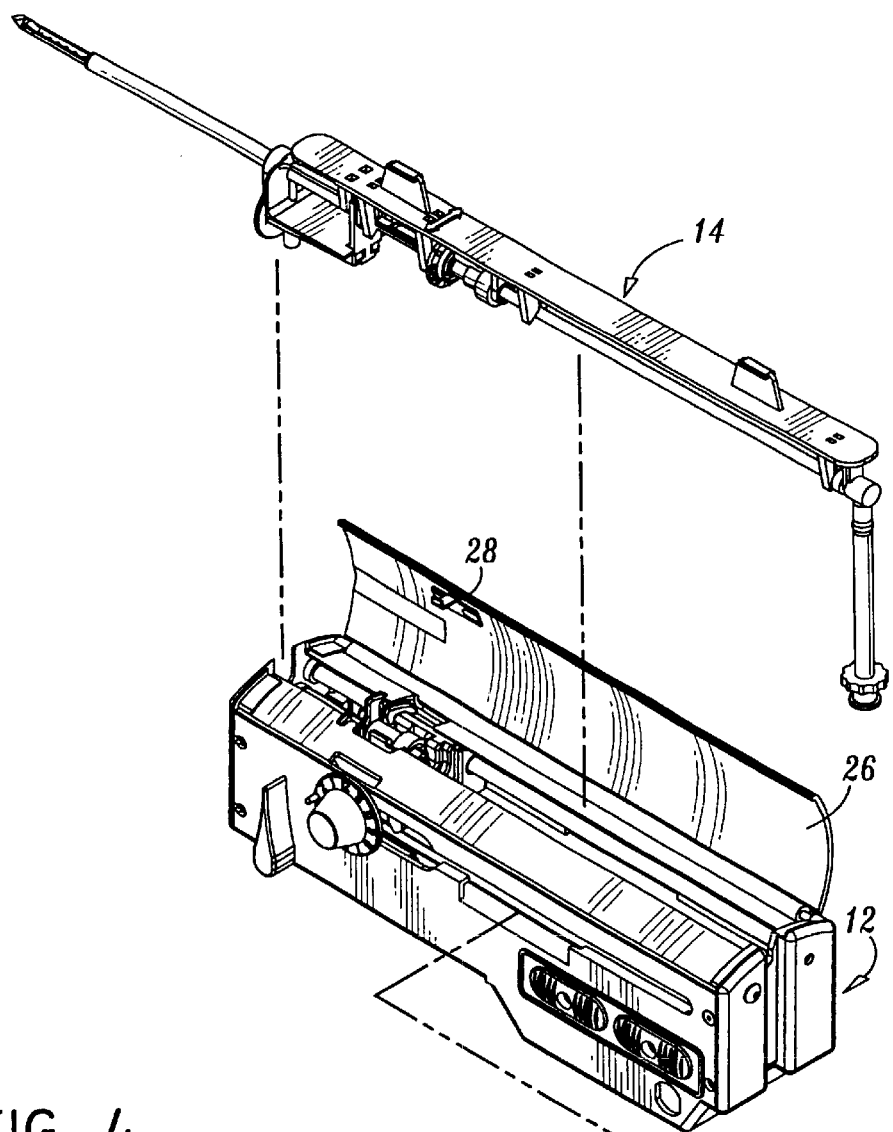
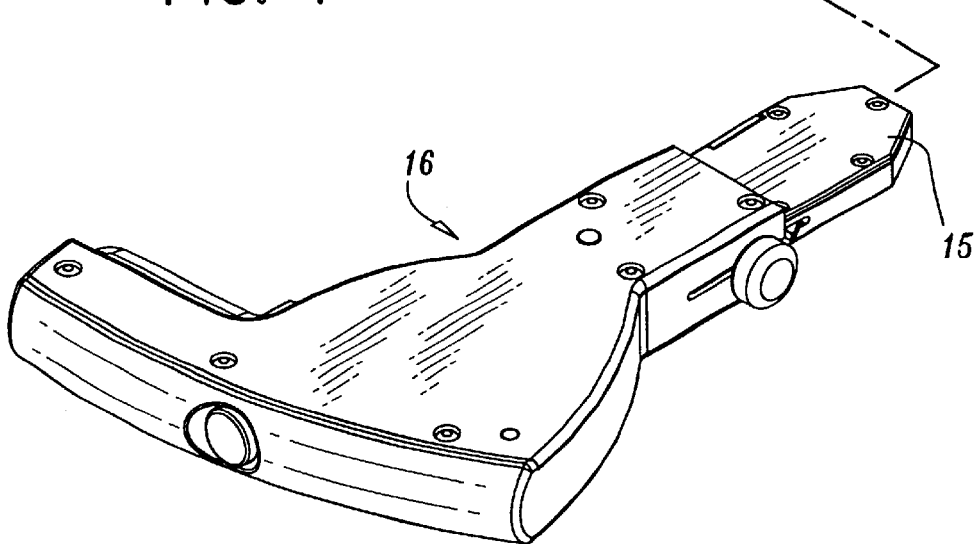
FIG. 4

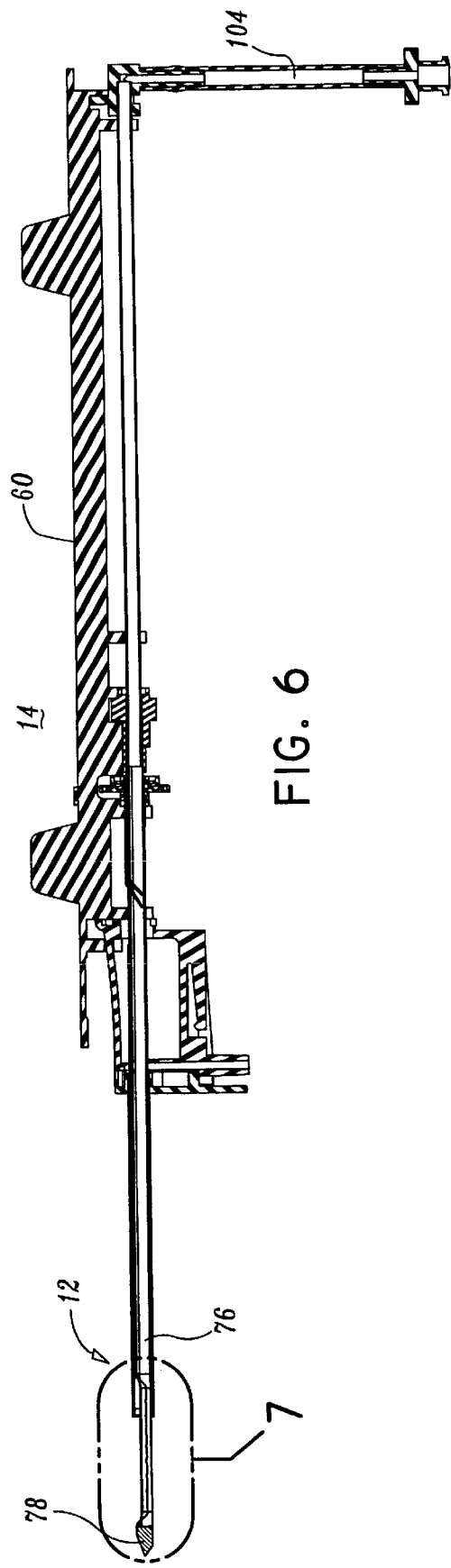
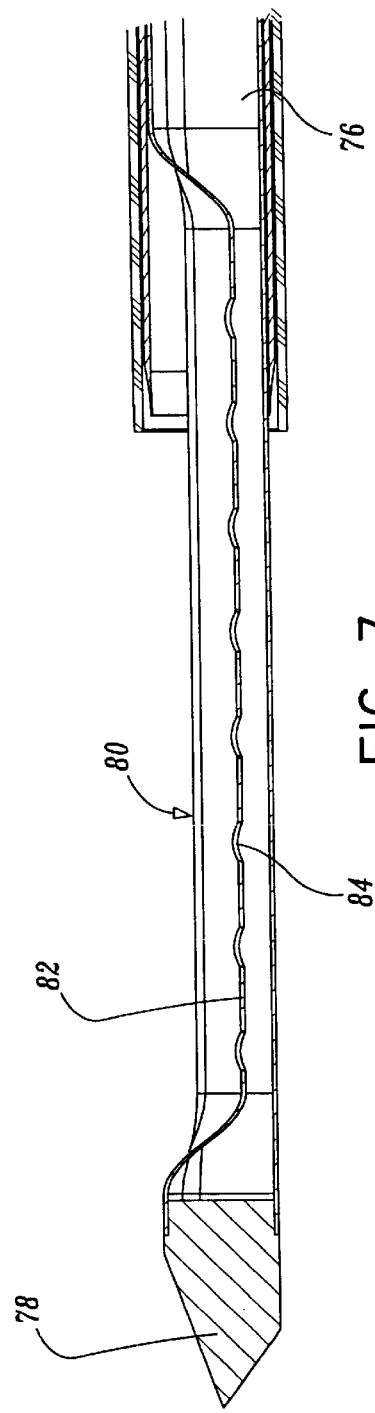
FIG. 6
FIG. 7

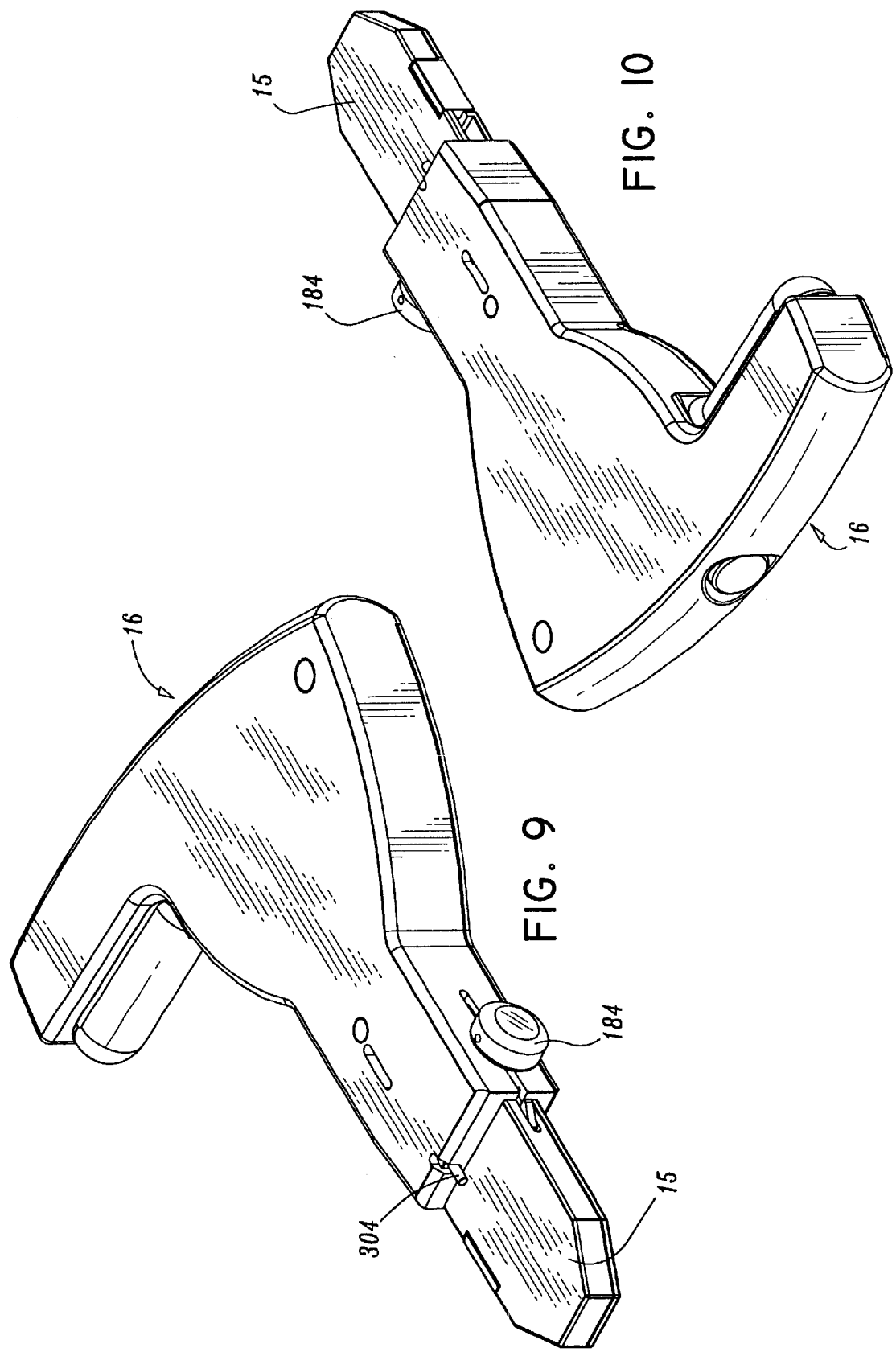

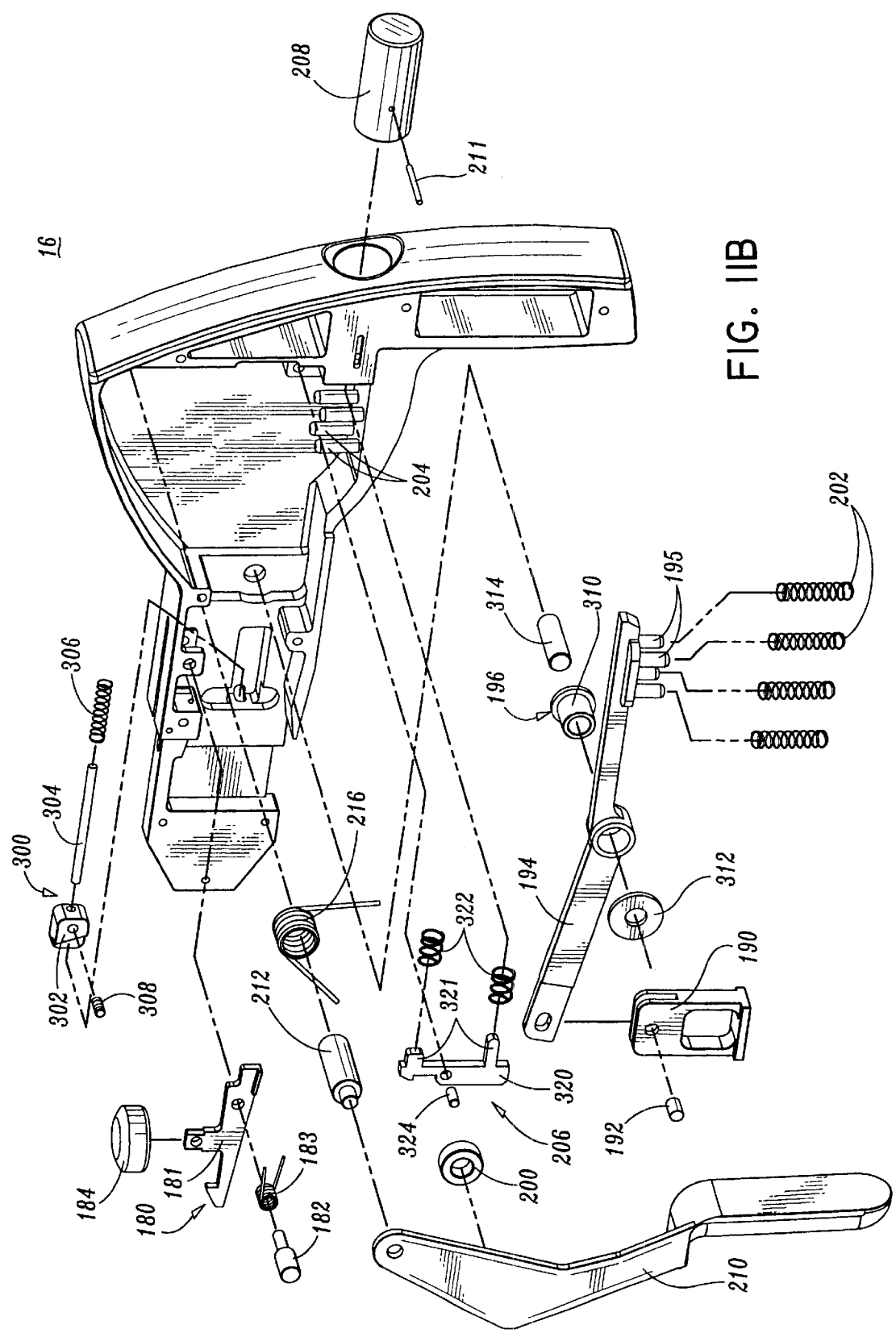
FIG. IIB

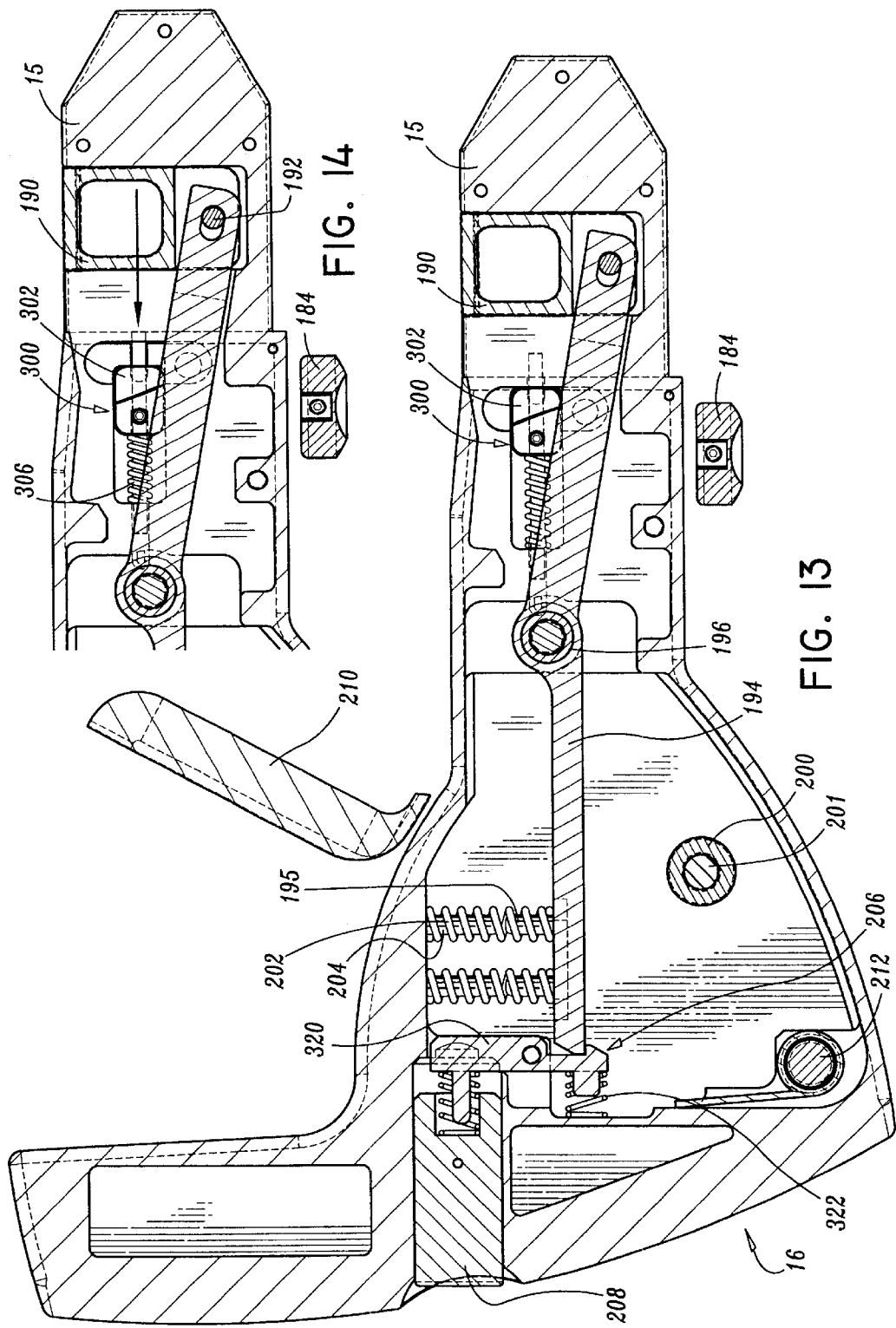

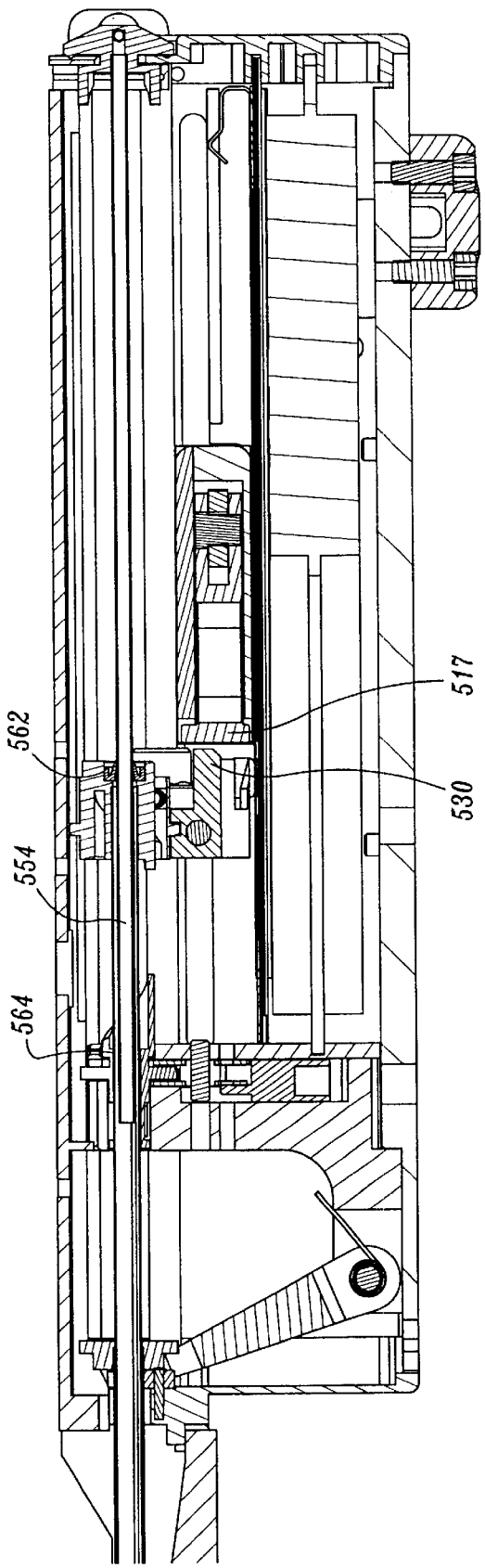
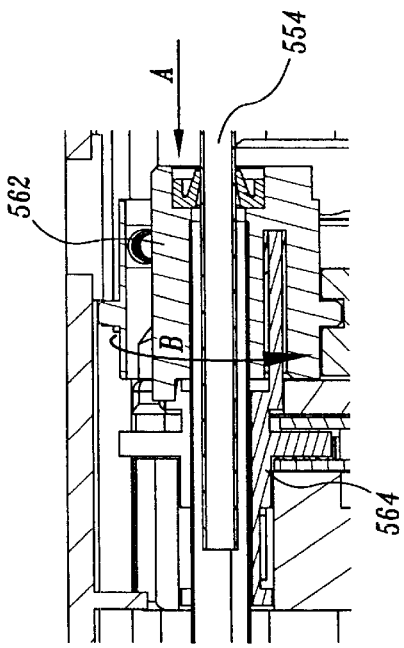
FIG. 31
FIG. 32

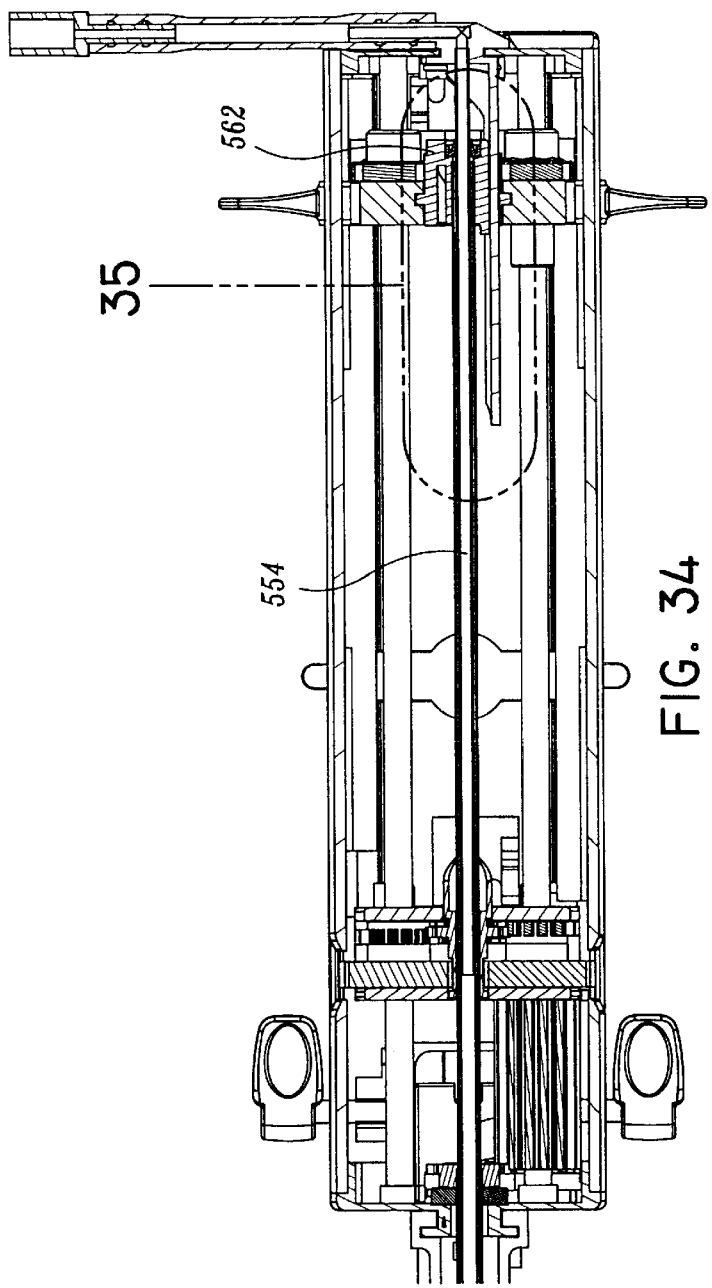
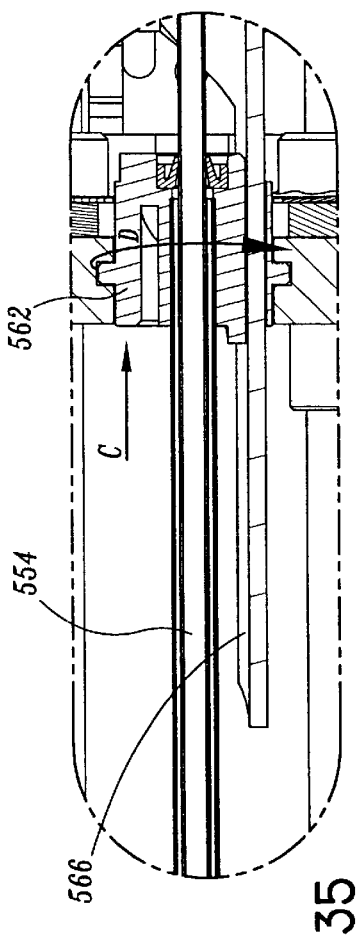
FIG. 34
FIG. 35

BIOPSY SYSTEM

CROSS-REFERENCE TO RELATED APPLICATIONS

This application claims priority to U.S. Provisional Application Serial No. 60/109,989 filed Nov. 25, 1998 by Viola et al. and U.S. Provisional Application Serial No. 60/158,667 filed Oct. 8, 1999 by Viola et al., the entire contents of each of these applications are hereby incorporated by reference.

BACKGROUND

1. Technical Field

This disclosure relates to a system and method for the biopsy of tissue specimens and, more particularly, to a single insertion, multiple sample percutaneous biopsy system and method.

2. Background of Related Art

It is often necessary to sample tissue in order to diagnose and treat patients suspected of having cancerous tumors, pre-malignant conditions and other diseases or disorders. Typically, in the case of suspected cancerous tissue, when the physician establishes by means of procedures such as palpation, x-ray or ultrasound imaging that suspicious conditions exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment tissue is obtained for histologic examination and can be performed via frozen section or paraffin section. In more recent developments, percutaneous techniques have been used to remove the entire mass during the initial procedure.

The type of biopsy utilized depends in large part on the circumstances present with respect to the patient and no single procedure is ideal for all cases. Core biopsy, however, is extremely useful in a number of conditions and is being used more frequently.

Intact tissue from the organ or lesion is preferred by medical personnel in order to arrive at a definitive diagnosis regarding the patient's condition. In most cases, only part of the organ or lesion need be sampled. The portions of tissue extracted must be indicative of the organ or lesion as a whole. In the past, to obtain adequate tissue from organs or lesions within the body, surgery was performed so as to reliably locate, identify and remove the tissue. With present technology, medical imaging equipment such as stereotactic x-ray, fluoroscopy, computer tomography, ultrasound, nuclear medicine and magnetic resonance imaging, may be used. These technologies make it possible to identify small abnormalities even deep within the body. However, definitive tissue characterization still requires obtaining adequate tissue samples to characterize the histology of the organ or lesion.

Mammography can identify non-palpable (not perceptible by touch) breast abnormalities earlier than they can be diagnosed by physical examination. Most non-palpable breast abnormalities are benign but some are malignant. When breast cancer is diagnosed before it becomes palpable, breast cancer mortality can be reduced. It is still difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope.

The introduction of stereotactic guided percutaneous breast biopsies offered alternatives to open surgical breast biopsy. With time, these guidance systems have become more accurate and easier to use. Biopsy guns were introduced for use in conjunction with these guidance systems.

Biopsy devices used in connection with the above-mentioned guidance systems, particularly those used for diagnostic procedures, suffered from various drawbacks. These devices are manufactured for use with a specific guidance system. Use with other systems requires modifications and adaptations to the biopsy device.

Use of current devices can be limited due to their length. Current designs may be too long or contain configurations for particular mammography tables. Therefore, the above-mentioned devices may not be usable with more than one guidance system without modification or may not be adaptable at all.

In many biopsy procedures, it is necessary to retrieve samples from different orientations at a tissue site. Another disadvantage of current devices is the inability to recall at what position a previous sample was taken. Another drawback suffered by current devices is severing tissue with a knife that is hand driven. This results in inconsistent sample size due to resilient tissue that may be encountered. Further, the firing of a biopsy gun and manipulation of a biopsy device into tissue may cause undesired collateral damage to untargeted tissue and surrounding bodily structures which may result in poor tissue sampling.

Therefore, a continuing need exists for percutaneous biopsy apparatus which can reliably extract adequate biopsy sample(s) with a single insertion of the biopsy instrument and has the versatility to be used in conjunction with various guidance systems used for retrieving tissue samples without the necessity of extensive modifications or adaptations. Preferably, such an apparatus provides an accurate and precise location and retrieval of tissue samples with minimized collateral damage to untargeted tissue and surrounding bodily structures. The apparatus may include the ability to recall sample retrieval position. The apparatus may also include the ability to control the rate for severing a sample. Most preferably, ergonomic enhancements are included for facile manipulation of the apparatus.

SUMMARY

The present disclosure describes systems and methods for the biopsy of tissue specimens, and more particularly, to a single insertion multiple sample percutaneous biopsy system that has the versatility to be used in conjunction with various types and sizes of imaging guidance systems, for example, prone table systems and upright sitting systems, used for retrieving tissue samples without the necessity of modifications or adaptations. The system, preferably, provides an accurate and precise location and retrieval of tissue samples with minimized collateral damage to untargeted tissue and surrounding bodily structures. Most preferably, ergonomic enhancements are included for facile manipulation. The versatility of the system is provided, at least in part, by its novel design and configuration.

The system is used in connection with vacuum assisted biopsy, which can be used for diagnosis. The system allows an operator to extract multiple samples of suspect tissue without withdrawing the active biopsy instrument from a patient to retrieve each separate tissue sample. The disclosed system and methods provide little or no need for stitches and the patient may resume normal activities almost immediately.

In one embodiment, in accordance with the present disclosure, a biopsy system, such as, for example, a biopsy apparatus is provided which includes a carriage housing defining a cavity therewithin. A biopsy instrument, such as, for example, an insertion unit is supported within the cavity of the housing. A firing module engages a wall of the housing and operatively engages the insertion unit for delivering a vacuum tube, defining a fluid passageway therein and a tissue basket, of the insertion unit towards a targeted tissue site. A tissue stripping member is disposed on the vacuum tube. The insertion unit may be disposable and suitable for various types of housings.

A tubular knife member is included within the insertion unit and is rotatably and reciprocatingly coaxially disposed about the vacuum tube. The tubular knife member has a cutting edge for severing tissue. An outer tube is included which is, preferably, made from a radiolucent material and coaxially disposed about the tubular knife member. The outer tube may include a radiopaque marker disposed thereon.

The housing may include a cover for maintaining the insertion unit within the cavity. A cover latch assembly may be provided and mounted to the housing. The housing may include wheel knobs for proper calibration and positioning of carriages for support of the insertion unit. Preferably, a latch and a lock cooperate with the wheel knobs to maintain the carriages in position.

The carriage housing may include a knife carriage for supporting the tubular knife member of the insertion unit. A knife advance assembly is, preferably, included to bias the tubular knife member between a range of motion for enhanced ergonomic control. A trocar carriage may be included in the carriage housing for support of the vacuum tube. Preferably, the trocar carriage is driven towards the tissue sample site by a ram of the firing module.

In another embodiment, the firing module has a module latch assembly for releasably engaging the firing module with the carriage housing. The module latch assembly includes a release button to release the firing module from the carriage housing. A firing release assembly is included to prevent firing of the hammer when the firing module is disengaged from the housing. A ram is included which is mounted to a rocker arm facilitating motion of the ram. The rocker arm can be actuated by springs. A trigger button engages a latch assembly that releases the rocker arm. The rocker arm causes the ram to drive the insertion unit into a lesion of a patient.

In a further alternative embodiment, a biopsy system, in accordance with the present disclosure is provided. The biopsy system includes a housing and a biopsy instrument operatively associated with the housing. The biopsy instrument is configured and dimensioned to remove a tissue sample from a patient. The biopsy instrument may include a tissue receiving portion. A firing module similar to that previously noted is detachably engageable with the housing and operatively associated with the biopsy instrument to facilitate selective rapid advancement of at least a portion of the biopsy instrument toward a targeted location with the patient. The biopsy system is adaptable to fit on an upright diagnostic biopsy table. Further, the biopsy instrument can be removable from the biopsy system.

The system may include an indexing assembly disposed within the housing and configured to cooperate with the biopsy instrument to selectively orient the tissue receiving portion. The biopsy instrument can include a tubular member cooperating with the tissue receiving portion. The indexing assembly includes a camming assembly disposed on the tubular member. The camming assembly may include a first cam member mounted to the tubular member. The first cam member is configured to engage a second cam member disposed within the housing. The first cam member is also configured to engage a third cam member disposed within the housing.

The indexing assembly may include a manual gearing assembly configured for selective orientation of the tissue receiving portion. The biopsy instrument may alternatively include a tubular member having a tissue receiving portion disposed near a distal end thereof. The biopsy instrument can further include a tubular knife member coaxially disposed relative to the tubular member and configured for actuation relative to the tubular member for severing tissue.

A linear advancement control assembly can be disposed within the housing and configured to effect linear actuation of the tubular knife member. The linear advancement control assembly may include a plurality of bearings mounted within the housing and configured to effect linear movement of the tubular knife member. The plurality of bearings may include three bearings oriented relative to each other such that the tubular knife member may be snap fit in between two of the bearings. The plurality of bearings may be oriented and configured such that contact surfaces of the respective bearings form a partially helical thread which effects axial translation of the tubular knife member.

An optical sensor may be disposed adjacent a portion of the tubular knife member and oriented to detect the orientation of a lateral opening formed through the tubular knife member. A carriage may be slidably disposed within the housing and configured to releasably retain at least a portion of the biopsy instrument within the housing.

In another alternative embodiment, the biopsy system includes a housing and a biopsy instrument operatively associated with the housing. The housing includes a first tubular member having a tissue basket formed near a distal end thereof. The tissue basket is configured for retrieval of tissue. The biopsy instrument further includes a tubular knife member coaxially disposed relative to the first tubular member and configured for cooperative movement with the first tubular member to sever a tissue sample from a patient. An indexing assembly is operatively engageable with the biopsy instrument for selective orientation of the tissue basket.

A method of performing a surgical biopsy is disclosed including the steps of inserting a biopsy apparatus, as described above, into tissue of a patient at a first tissue sampling site, applying suction to the tissue basket to draw tissue into the tissue basket, severing the tissue from the first tissue sampling site by actuating the tubular knife member of the biopsy instrument, retracting the tissue basket from the first tissue sample site for removal of tissue from the tissue basket such that a cam being disposed on the first tubular member interacts with a cam assembly disposed within the housing to orient the tissue basket to a predetermined orientation, and removing tissue from the first tissue sampling site from the tissue basket remote from the first tissue sampling site. The method may further include the step of returning the tissue basket to the first tissue sampling site as determined by the indexing assembly. The method may further include the step of orienting the tissue basket at a second tissue sampling site as determined by the indexing assembly. The method may further include the step of applying suction to the tissue basket to draw tissue into the tissue basket. The method may still further include the step of severing tissue from the second tissue sampling site by actuating the tubular knife member. The method may further include the step of retracting the tissue basket from the second tissue sampling site for removal of tissue from the second tissue sampling site.

In yet another alternative embodiment, the biopsy system includes a disposable biopsy instrument kit which includes a biopsy instrument including at least two coaxially disposed tubular members movable relative one another to sever a discrete tissue sample from a patient and an alignment member removably attached to the biopsy instrument. The alignment member retains the at least two coaxially disposed tubular members in a fixed relative position and orientation with respect to each other.

In another embodiment, the biopsy instrument includes a drive apparatus having a housing and a carriage assembly slidably disposed within the housing. The carriage assembly is adapted to receive and removably retain a biopsy instrument. A firing module is detachably engageable with the housing and operatively associated with the carriage assembly to facilitate selective rapid linear advancement of the carriage assembly.

BRIEF DESCRIPTION OF THE DRAWINGS

Various embodiments of the present disclosure are described herein with reference to the drawings, wherein:

FIG. 3 is an enlarged perspective view of a forward end of the biopsy apparatus of FIG. 1;

FIG. 3A is an enlarged perspective view of an H-latch;

FIG. 3B is an enlarged perspective view of a forward end of the biopsy apparatus from the opposite perspective of FIG. 3;

FIG. 3C is an enlarged perspective view of a knob wheel for engaging a knob lock;

FIG. 4 is a perspective view of the biopsy apparatus of FIG. 1 with the three main components separated;

FIG. 6 is a side cross-sectional elevation view of the insertion unit;

FIG. 7 is an enlarged cut-away section of the indicated area of detail of FIG. 6, which shows the distal portion of the insertion unit;

FIG. 9 is a perspective view of one embodiment of a firing module portion of the biopsy apparatus;

FIG. 10 is a perspective view of the reverse side of the embodiment shown in FIG. 9;

FIG. 11B is a perspective view with parts separated of the firing module embodiment of FIG. 9;

FIG. 13 is an enlarged side view in cross-section illustrating a reverse angle of the embodiment shown in FIG. 12;

FIG. 14 is an enlarged side view in cross-section of the insertion end of the embodiment shown in FIG. 13, illustrating the operation of a firing safety mechanism;

FIG. 31 is an enlarged side view of a portion of the biopsy system shown in FIG. 17;

FIG. 32 is an enlarged cut-away section of the indicated area of detail of FIG. 31;

FIG. 34 is a top cross-sectional view of the biopsy system shown in FIG. 33 taken along section line 34—34;

FIG. 35 is an enlarged cut-away section of the indicated area of detail of FIG. 34;

DETAILED DESCRIPTION OF EXEMPLARY EMBODIMENTS

The present disclosure is directed to a biopsy system and method for the biopsy of tissue specimens and, more particularly, to a single insertion multiple sample percutaneous biopsy system and method.

Figure 1:
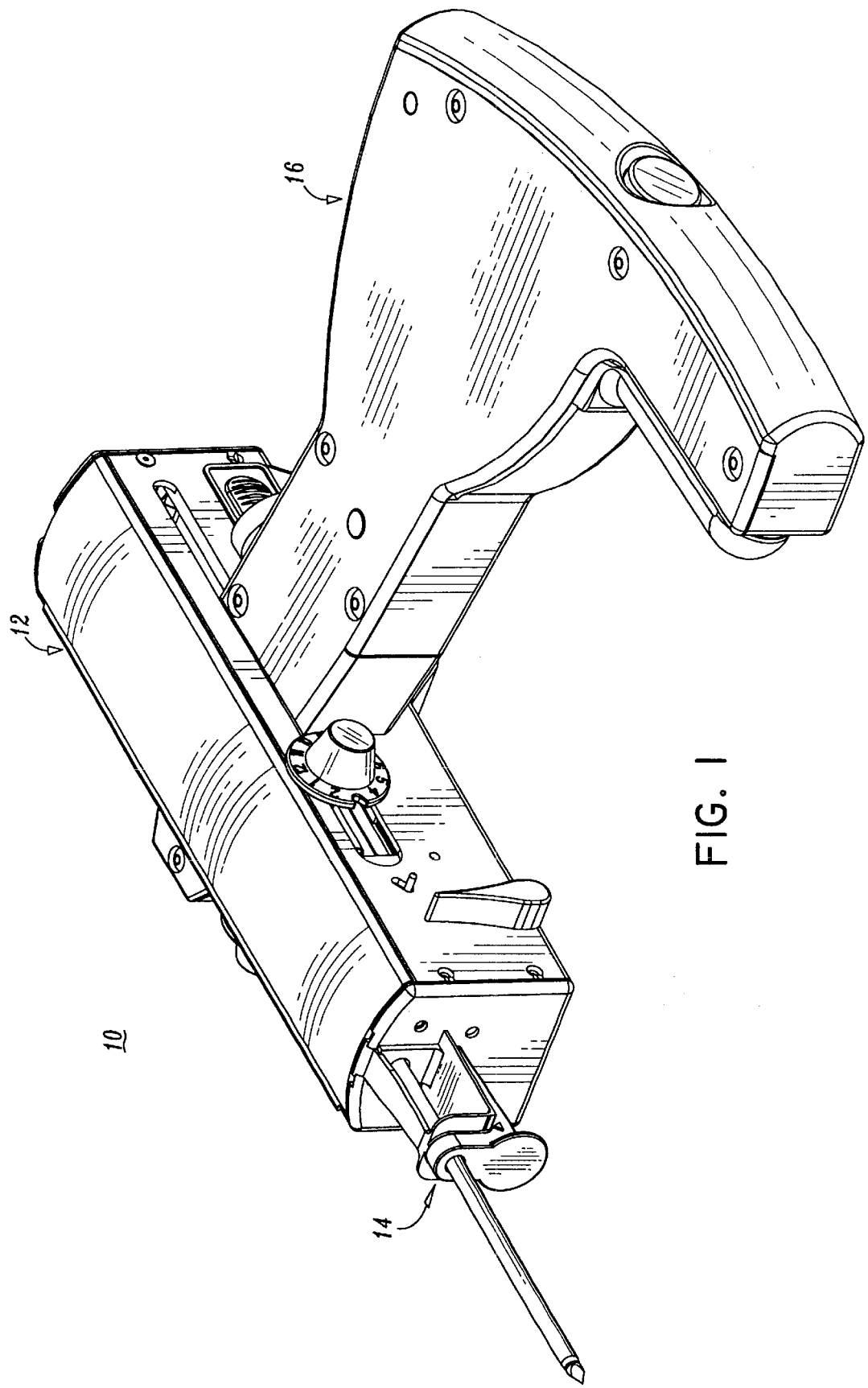
FIG. 1 is a perspective view of one embodiment of a biopsy apparatus constructed in accordance with the principles of the present disclosure.

In general, as shown in FIG. 1, the biopsy system hereinafter referred to as biopsy apparatus 10 includes a carriage housing 12, a biopsy instrument, such as, for example, insertion unit 14, and a firing module 16. These elements of the apparatus cooperate to facilitate retrieval of multiple tissue specimens wherein insertion unit 14 includes a vacuum tube 76 having a tip portion, such as, for example, a penetrating tip 78 and a lateral opening, such as, for example, a tissue basket 80 that is introduced into a target mass in a patient's breast. Suction is applied which is communicated to an area adjacent tissue basket 80 to a vacuum plate, such as, for example, a tissue support plate 82 to draw at least a portion of the target tissue mass into tissue basket 80. A knife tube 64 is advanced distally around the outside of vacuum tube 76 while rotating, in order to sever the target tissue portion from the surrounding tissue mass.

Once the target tissue portion is severed, vacuum tube 76 with penetrating tip 78 is retracted through knife tube 64 in order to remove the sample. In particular, upon retraction, tissue basket 80 is exposed adjacent to a tissue receptacle location. Retraction of vacuum tube 76 to the tissue receptacle location brings a tissue stripper plate 110 into tissue support plate 82 contact with the target tissue portion, removing it from and preferably causing it to fall into a receptacle. Alternatively, stripper plate 110 may be omitted and the tissue retrieved by way of conventional methods, for example, grasping with forceps. A detailed explanation of retrieval of the target tissue portion, for example, is provided in U.S. patent application Ser. No. 09/040,244 filed Feb. 20, 1998 by David Faracioni et al., the entire contents of which are hereby incorporated by reference.

Referring now in specific detail to the drawings in which like reference numerals identify similar or identical elements throughout the several views, and initially to FIG. 1, one preferred embodiment is shown generally as biopsy apparatus 10. As noted above, biopsy apparatus 10 includes a carriage housing 12, an insertion unit 14 and a firing module 16. Referring temporarily to FIG. 4, insertion unit 14 is received and supported within carriage housing 12 for operative engagement therewith. Firing module 16 is laterally received within an opening formed in carriage housing 12 for operative engagement with carriage housing 12 and insertion unit 14.

Figure 2:
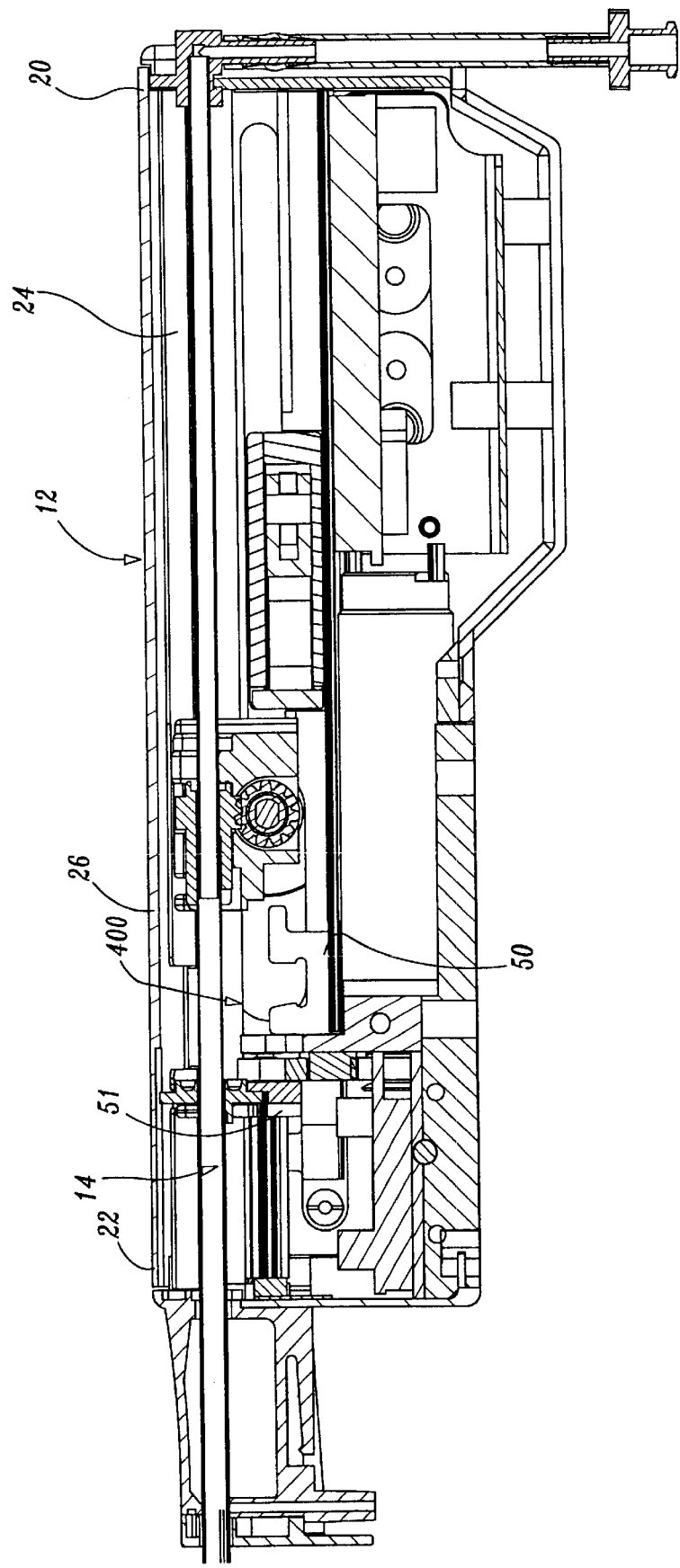
FIG. 2 is an enlarged side cross-sectional view in elevation of a portion of the biopsy apparatus of FIG. 1.

As shown in FIG. 2, carriage housing 12 extends axially from a proximal end 20 to a distal end 22 and defines a cavity 24 therewithin for support of insertion unit 14 and receipt of firing module 16 (FIG. 1). Preferably, carriage housing 12 includes a drive unit and system controls elements of insertion unit 14. An example of a drive unit and system controls is disclosed in U.S. Provisional Application Serial No. 60/078,748, entitled "Biopsy Instrument Driver Apparatus" filed on Feb. 20, 1998, the entire contents of which are hereby incorporated by reference.

Referring to FIGS. 2–4, carriage housing 12 includes a cover 26 hingedly attached to carriage housing 12 to maintain insertion unit 14 within housing 12. Cover 26 includes tabs 28 mounted thereon for receiving and maintaining an H-latch 30, as shown in FIG. 3A, mounted to cover 26. H-latch 30 includes a foot 32 for cooperating with a cover latch assembly 34 included within carriage housing 12, as shown in FIG. 3, for maintaining cover 26 in a closed position.

Cover latch assembly 34 includes an outer latch 36 and an inner latch 38. Outer latch 36 and inner latch 38 cooperate with foot 32 of H-latch 30 to maintain cover 26 in a closed position. Housing 12 further includes wheel knob 40 for orientation of a tissue basket of insertion unit 14. Wheel knob 40 is adjusted using an analog clock configuration to rotate a vacuum tube 76 (FIG. 7) of insertion unit 14. It is contemplated that various incremental configurations may be used to manipulate the positioning of insertion unit 14.

Wheel knob 40 cooperates with cover latch assembly 34 to maintain wheel knob 40 in the "12 o'clock" position while cover 26 is in the open position. As shown in FIGS. 1 and 3, inner latch 38 may include a pin 230 to engage wheel knob 40 in the "12 o'clock" position while cover 26 is in the open position. In the open position a shaft 56 to which wheel knob 40 is attached engages latch assembly 34.

As illustrated in FIG. 3B, carriage housing 12 includes a knob lock 50. Knob lock 50 is resiliently biased in an upward direction. Knob lock 50 may be directed downward by a cam 51, preferably, mounted to cover 26. As cover 26 is manipulated to an open position, knob lock 50 is directed upward by cam 51. Knob lock 50 defines channel 53 for receipt and locking of a rear wheel knob 54. Rear wheel knob 54 has a flat 55 to engage channel 53. Wheel knob 40 and rear wheel knob 54 are positioned in carriage housing 12 in a generally parallel orientation and attached by a shaft 56, shown in FIG. 3.

Carriage housing 12 further includes knife tube control 42, shown in FIGS. 3 and 3B, for controlling movement of a knife tube 64 from either side (FIG. 8 and described herein below) of insertion unit 14. Knife tube control 42 includes a pair of manual knobs 46, one disposed on each side of insertion unit 14, for controlling advancement and retraction of knife tube 64. Manual knob 46 is rotatable through a range of motion which biases between selected range limits. Preferably, manual knob 46 has a range of motion that includes a stroke of approximately 60°. Most preferably, knife advance assembly 42 includes a cam face with a ball bearing assembly on a lever arm so that a load increases gradually to a maximum threshhold at an over center position providing enhanced ergonomic features for a more precise and facile control of knife tube 64.

Carriage housing 12 also includes a carriage assembly 400 shown in FIGS. 3 and 4, for receipt of insertion unit 14. Carriage assembly 400 includes a knife carriage 410 for receipt and supporting engagement of knife tube 64 and a trocar carriage 420 for receipt and supporting engagement of vacuum tube 76 (FIG. 3 and described herein below) of insertion unit 14.

Insertion unit 14, as shown in FIGS. 5 through 8, is supported within carriage housing 12. Insertion unit 14 includes a calibrator member such as a release strip 60, as best shown in the exploded view of FIG. 8, which maintains the elements of insertion unit 14 in the proper axial and rotational position for support within carriage housing 12. Release strip 60 is configured so that insertion unit 14 may be positioned within carriage housing 12 in one orientation only, so that insertion unit 14 is properly calibrated or "registered" in conjunction with the alignment of wheel knob 40 for use.

Figure 5:
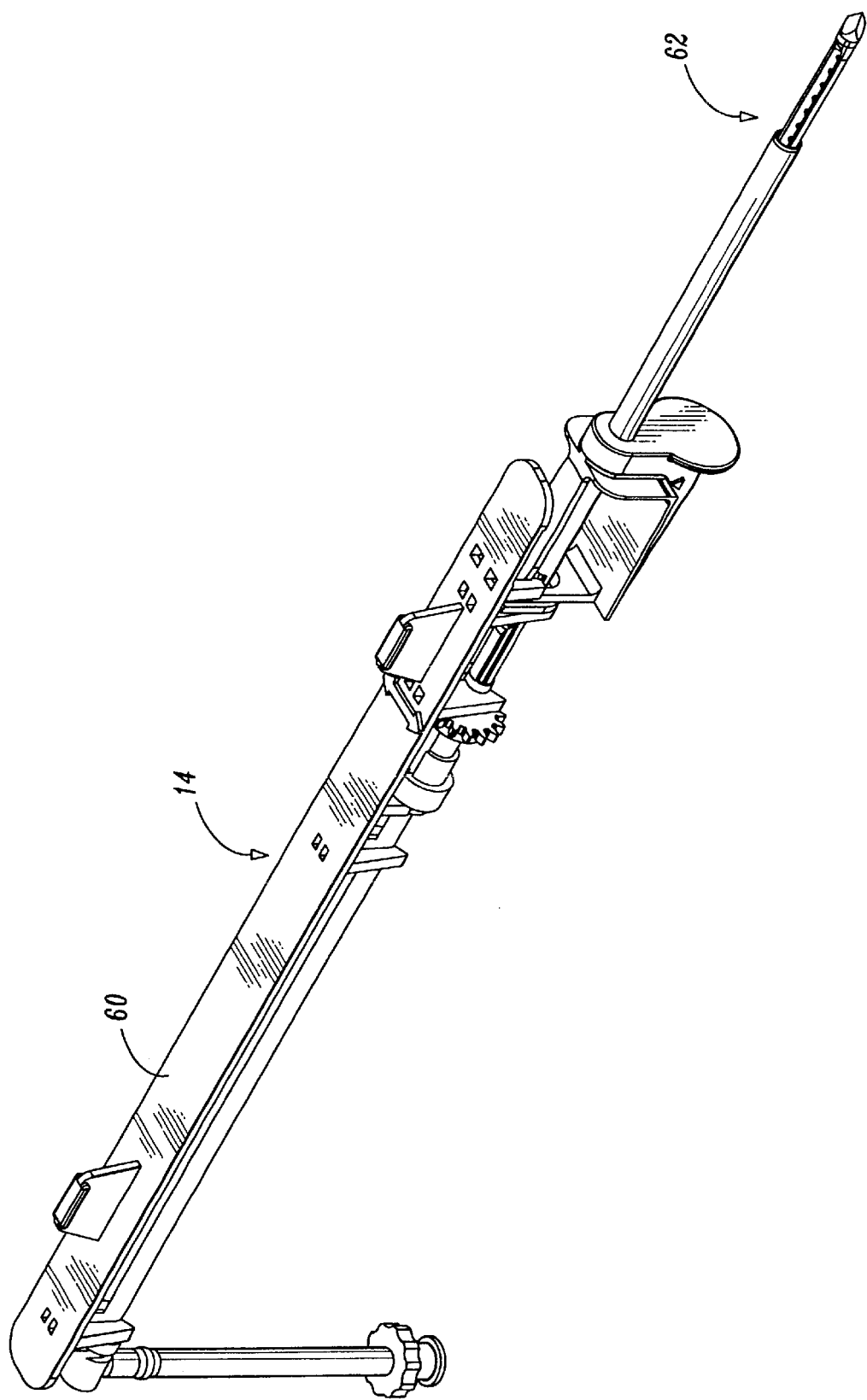
FIG. 5 is a perspective view of an insertion unit component of the biopsy apparatus of FIG. 1.

Insertion unit 14 is, preferably, a single use disposable loading unit meaning that it may be disposed after obtaining multiple biopsy specimens from a single insertion. Insertion unit 14 is adapted for attachment to reusable carriage housing 12. As shown in FIG. 5, insertion unit 14 includes an insertion end portion 62 configured and dimensioned for percutaneous introduction into a patient. Insertion end portion 62 extends from a distal end 22 of carriage housing 12.

Figure 8:
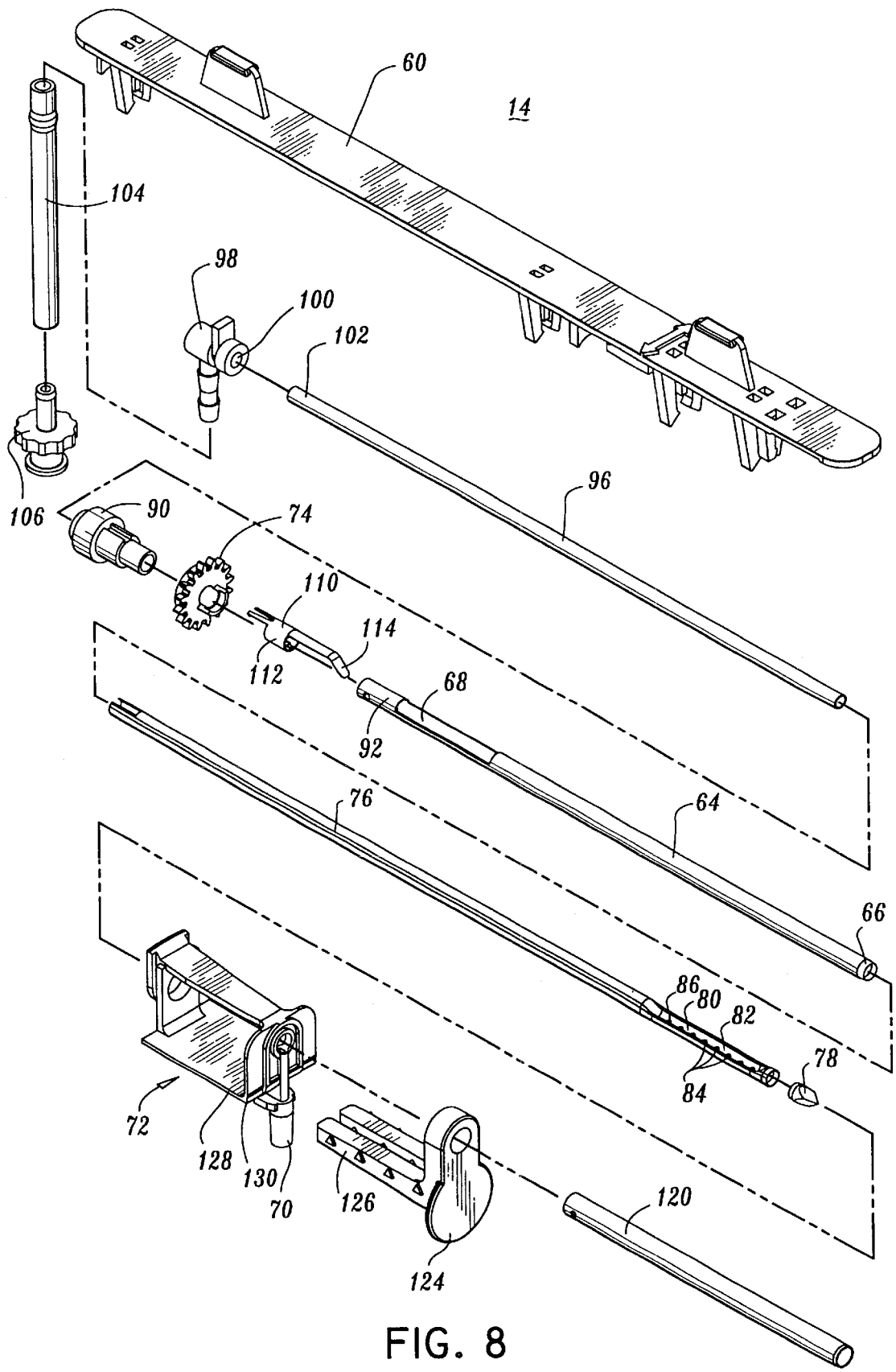
FIG. 8 is a perspective view of the insertion unit with parts separated.

Referring to FIG. 8, insertion unit 14 includes a series of concentrically disposed tubular members. The first such tubular member is a knife tube 64 which has a beveled angular cutting surface 66 formed at the distal end thereof and a laterally facing tissue discharge port 68 disposed proximally of annular cutting surface 66. To assist in the removal of fluids or the like, a laterally oriented vacuum port 70 is found adjacent the distal end of an insertion unit housing 72 and is, preferably, connected to a vacuum source (not shown) which may be actuated by the user.

A gear 74 is securely mounted onto knife tube 64. The assembled knife tube 64 is supported within carriage housing 12. Gear 74 meshes with a gear connected to a commercially available motor to rotate knife tube 64 at approximately 1200 rpm. Knife tube 64 is disposed within carriage housing 12 such that simultaneous rotational and longitudinal translational movement thereof is facilitated.

A vacuum tube 76 is concentrically disposed within knife tube 64 such that a penetrating tip 78 extends out the distal end of knife tube 64 beyond annular cutting surface 66. In this manner, penetrating tip 78 and knife tube 64 form a substantially continuous penetrating assembly for insertion into a patient's tissue, for example, a compressed breast. A tissue basket 80 is formed adjacent the distal end of vacuum tube 76. Tissue basket 80 faces laterally and is defined by a tissue support plate 82 which is provided with a series of vacuum holes 84 formed longitudinally therealong. A proximal-most vacuum hole 86 is formed a distance away from the series of holes 84. Vacuum hole 86 is provided to assist in sealing off the distal end of knife tube 64 to prevent too great a loss of vacuum force through apparatus 10 so that the remaining vacuum holes 84 can efficaciously pull the target tissue into tissue basket 80.

As shown in cross-section in FIGS. 6 and 7, tissue plate 82 is, preferably, arcuately shaped and secured to vacuum tube 76 by welding or the like having a substantially continuous surface depression formed near the distal end of vacuum tube 76. This arcuate or sinusoidal shape of tissue plate 80 in combination with the fact that knife tube 64 represents the outer most diameter of apparatus 10 at the point of insertion facilitates taking larger tissue samples than with other existing tissue sampling apparatus geometry.

Referring back to FIG. 8, a vacuum port adapter 90 securely mounts to a proximal end 92 of knife tube 64. Gear 74 cooperatively engages vacuum port adapter 90 about knife tube 64. Vacuum port adapter 90 securely mounts to vacuum line 96. A vacuum port 98 defines an opening 100 which securely mounts to a proximal end 102 of vacuum line 96. Vacuum port 98 is seated within a vacuum collar 104 in a fluid tight engagement. Vacuum collar 104 receives a vacuum connector 106. Vacuum connector 106 facilitates attachment of a vacuum hose (not shown) which is connected to a vacuum source (not shown) to provide a vacuum supply to vacuum line 96. Vacuum line 96 is in fluid communication with vacuum tube 76 and vacuum tube 76 is in fluid communication with tissue basket 80.

Extraction of a tissue sample from within tissue basket 80 is facilitated by a tissue stripping clip 110 which is in the form of a modified leaf spring having a collar portion 112 configured and dimensioned to slidably mount onto knife tube 64, in alignment with tissue discharge port 68. It is contemplated that collar portion 112 may also be opened sided. Tissue stripping clip 110 includes an inwardly deflected distal end portion 114 which is held to bias against the outer surface of vacuum tube 76 to facilitate stripping of the tissue sample upon retraction of vacuum tube 76 within knife tube 64. Tissue stripping clip 110 may additionally be provided with a coating material or lubricant to reduce the friction forces along the surface of tissue stripping clip 110 which may come into contact with the sample tissue being extracted. In this manner, the tissue would be more readily removed from tissue basket 80 with less likelihood of adherence to tissue stripping clip 110. Any suitable known friction-reducing coatings may be applied to tissue stripping clip 110 and/or tissue plate 82.

A radiolucent outer tube 120 is attached to a sliding clip 124 which provides removable attachment to housing 72 at the distal end thereof. Outer tube 120 is radiolucent so that it may be left at the tissue sampling cite for imaging of the suspect tissue without the presence of the radiopaque knife tube 64 and vacuum tube 76. Outer tube 120 is, preferably, provided with at least one radiopaque marking such as a peripheral line to indicate the longitudinal spacing of the sampling site in order to provide the user with an indication of the tissue sampling area.

Sliding clip 124 is provided with a pair of delectable legs 126 which fit within parallel receiving slots formed on the underside of housing 72. Receiving slots 128 are formed on the underside of housing 72. A pair of diamond shape camming surfaces 130 are formed along a wall portion on the underside of housing 72. Camming surfaces 130 act as temporary stops which resist longitudinal movement of sliding clip 124. Upon complete distal movement of sliding clip 124, the distal end of outer tube 120 is substantially aligned with the distal end portion of the location of tissue basket 80 at insertion in the target tissue mass thus providing a marker for the location of the tissue sampling site upon removal of apparatus 10 from the suspect tissue region.

Referring temporarily back to FIG. 5, insertion unit 14 includes an indicator arrow 150 for proper placement of insertion unit 14 within housing 12.

Referring now to FIGS. 9–16, firing module 16 will now be described in detail. As illustrated in FIGS. 9 and 10, firing module 16 is shown prior to engagement with apparatus 10. As shown in FIG. 4, an insertion end 15 of firing module 16 is laterally and slidably inserted within carriage housing 12.

Figure 11:
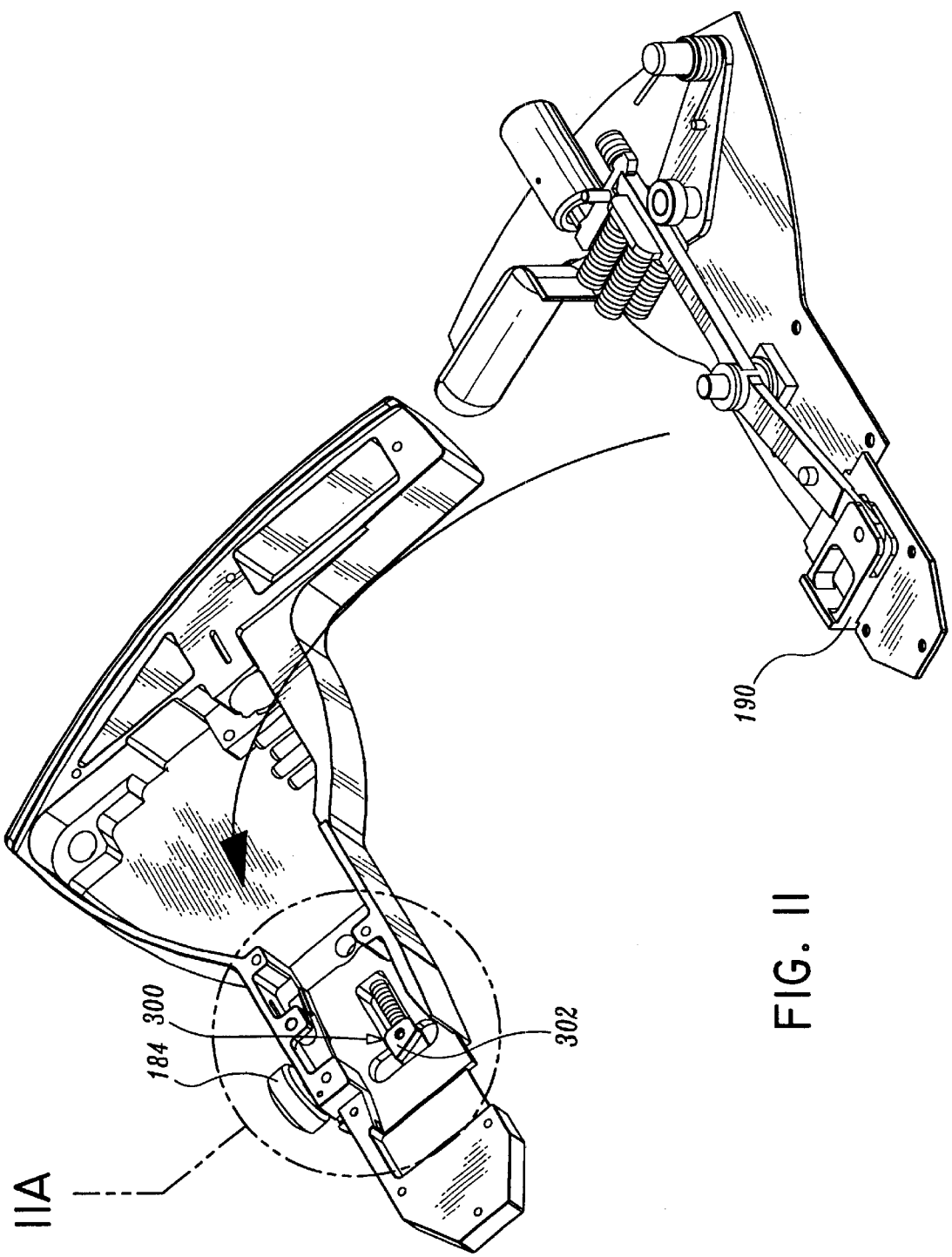
FIG. 11 is a perspective view with a cover plate separated to illustrate the functional elements of the firing module.
Figure 11A:
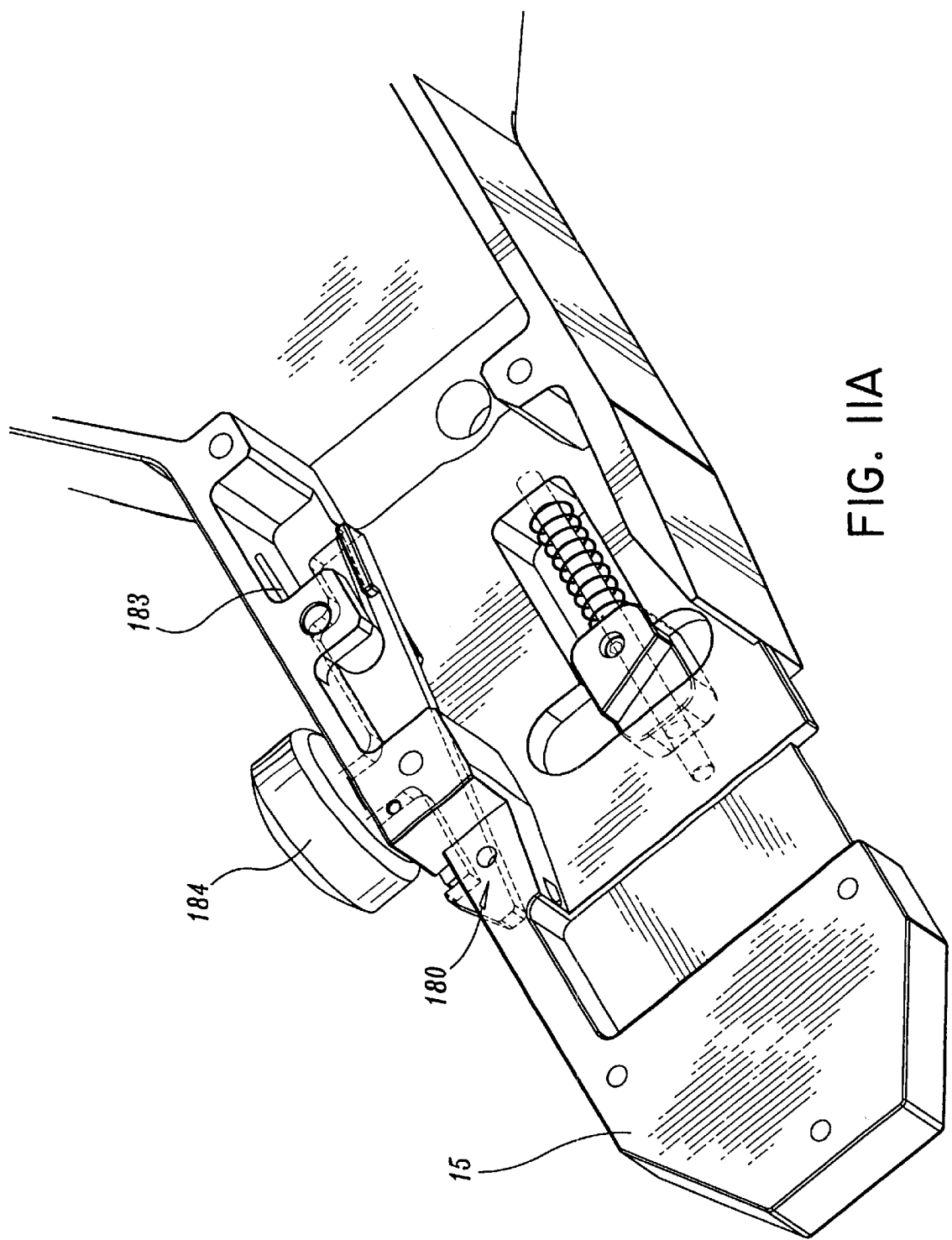
FIG. 11A is a cut-away section of the indicated area of detail of FIG. 11 showing one embodiment of the insertion end of the firing module.
Figure 12:
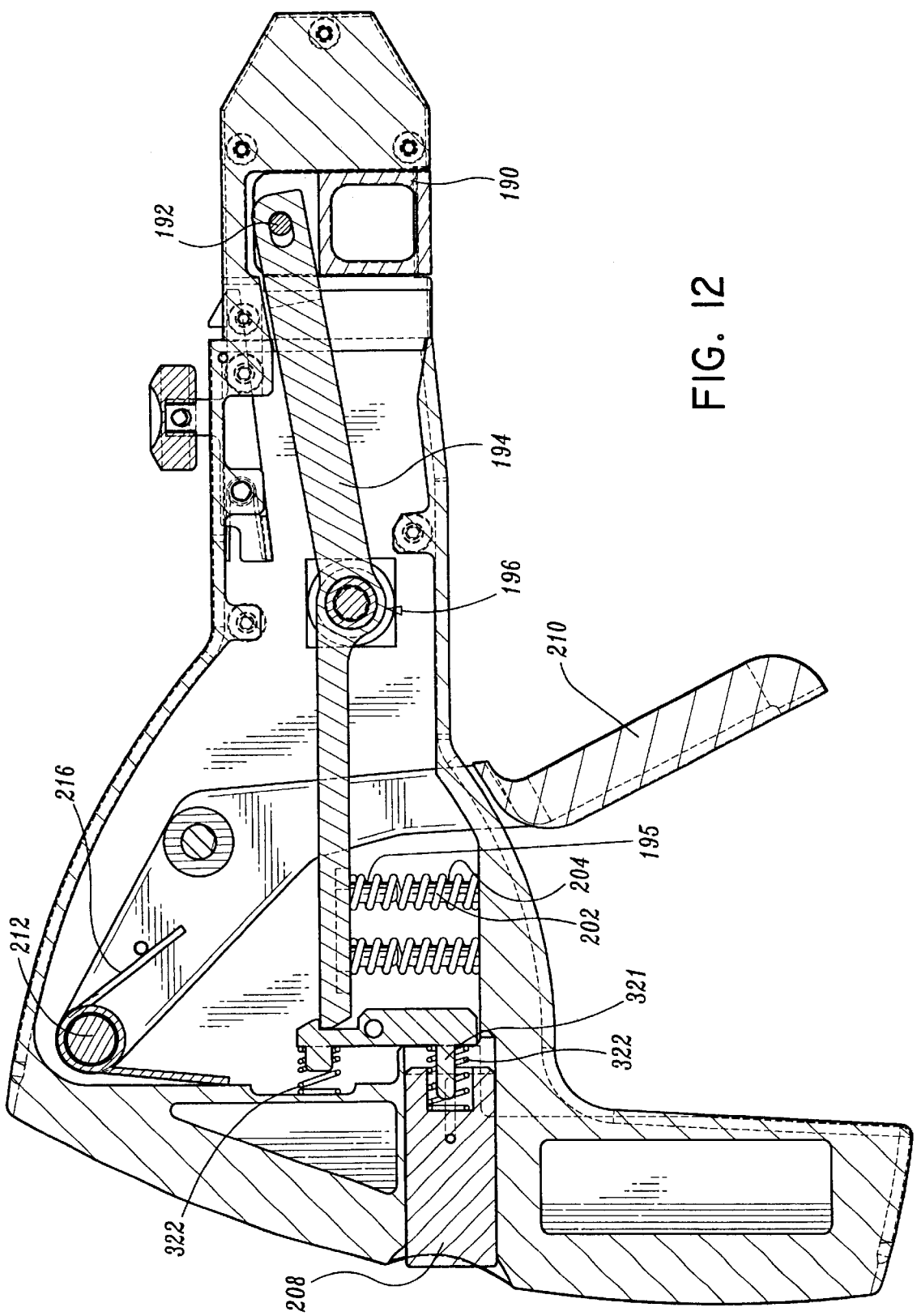
FIG. 12 is an enlarged side cross-sectional view of the firing module.

Firing module 16 includes a module latch assembly 180 that releasably secures firing module 16 to carriage housing 12, as shown in FIGS. 11, 11A and 11B. Latch interface 181 of module latch assembly 180 pivots about a pin 182 and is resiliently biased by a latch spring 183 in a counterclockwise direction to engage carriage housing 12. To release firing module 16 from carriage housing 12, module latch assembly 180 includes a latch release button 184 that is manually depressed to release firing module 16 from carriage housing 12.

As shown in FIGS. 11, 11B, 13 and 14, firing module 16 includes a firing safety mechanism such as release assembly 300 that prevents firing of a ram 190 when firing module 16 is disengaged from apparatus 10. Firing release assembly 300 includes a cam 302, a pin 304, a spring 306 and a latch pin 308. Cam 302 and spring 306 are supported by pin 304 and fixed by latch pin 308, pin 304 extending exterior from firing module 16 (FIG. 9). Firing release assembly 300 is resiliently biased in an axial direction by spring 306. Firing module 16 is inserted into carriage housing 12 and pin 304 is depressed forcing cam 302 rearward, permitting motion of ram 190, as shown in FIGS. 13 and 14.

As shown in FIG. 11B, firing module 16 includes ram 190 which is fixedly mounted by a ram pin 192 to a rocker arm 194. Rocker arm 194 is mounted to firing module 16 and pivots about bearing assembly 196, facilitating motion of ram 190. Bearing assembly 196 includes bearing flange 310, thrust washer 312 and bearing pin 314.

Firing module 16 further includes firing springs 202 for actuating rocker arm 194. Rocker arm 194 includes rocker rods 195 for supporting firing springs 202 thereon. Firing springs 202 are further supported on spring rods 204 which are fixedly mounted to firing module 16. Spring rods 204 and rocker rods 195 provide guided support for firing springs 202 into active engagement with rocker arm 194. A cocking latch release assembly 206 engages rocker arm 194 to maintain springs 202 in a compressed position over spring rods 204. This configuration provides the maximum potential energy within springs 202 which when released, provide a transfer of the maximum kinetic energy of springs 202 to rocker arm 194.

Cocking latch release assembly 206 includes a cocking latch 320 which is resiliently biased by cocking springs 322 about a pin 324. Cocking latch 320 rocks about pin 324 to release rocker arm 194 to fire ram 190. To release cocking latch 320 from engagement with rocker arm 194, a trigger button 208 is depressed. Trigger button 208 is mounted by pin 211 to firing module 16 and resiliently biased against cocking latch 320 by cocking springs 322. Cocking springs 322 are supported on latch 320 by latch legs 321. Firing module 16 may be reset or re-cocked using cocking arm 210 to compress springs 202 to a maximum potential energy position in engaging contact with rocker arm 194.

Figure 15:
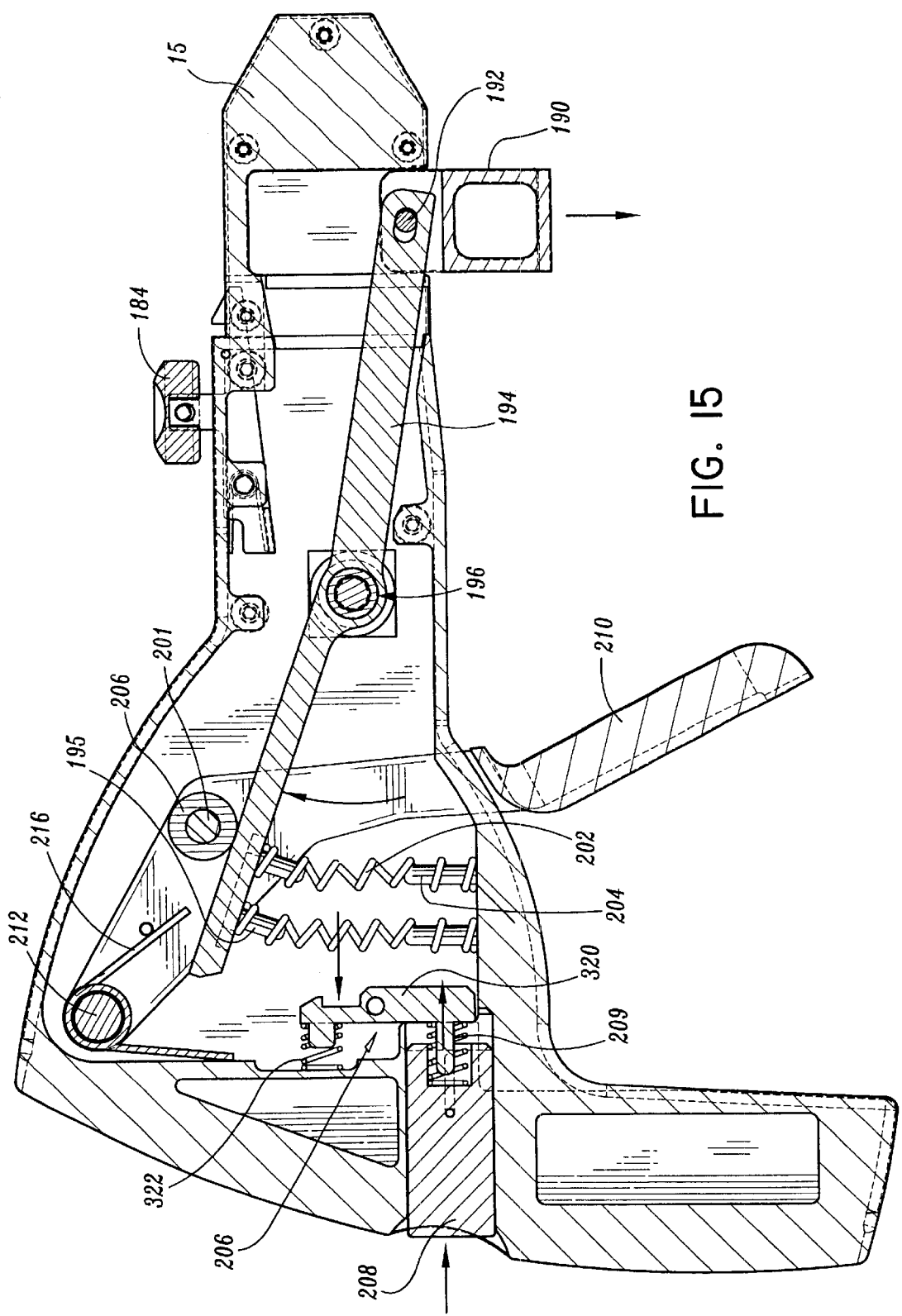
FIG. 15 is an enlarged side view in cross-section showing actuation of the firing module.
Figure 16:
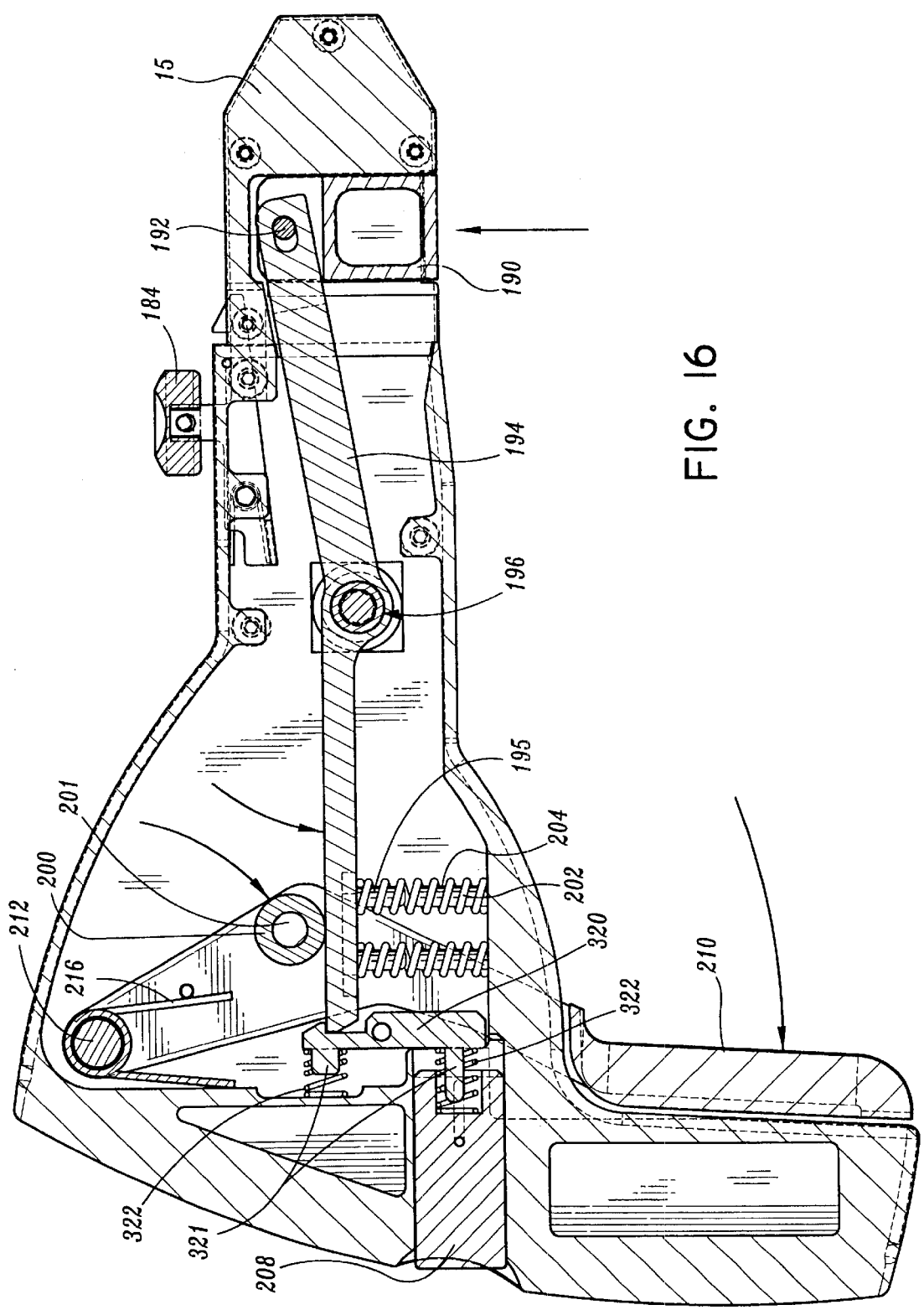
FIG. 16 is an enlarged side view in cross-section showing operation of the reset mechanism of the firing module.

Cocking arm 210 is mounted to firing module 16 and pivots about cocking arm pin 212. Cocking arm 210 is resiliently biased in a counter-clockwise direction about pin 212 by arm spring 216, as best shown in FIGS. 15 and 16. Cocking arm 210 further includes a cocking bearing 200 supported by bearing pin 201. As shown in FIG. 15, in the un-cocked position, bearing 200 contacts rocker arm 194. Cocking arm 210 is manipulated in a clockwise direction (as viewed in the perspective of FIG. 16) whereby bearing 200 forces rocker arm 194 into engagement with cocking latch release assembly 206 and into a reset orientation. Cocking of rocker arm 194 forces a camming motion with latch 320 which thereby resets trigger button 208 so that firing module 16 may be fired forcing ram 190 to drive insertion unit 14. Firing module 16 may be slidably received in either side of carriage housing 12.

Referring now to FIGS. 13–16, the operation of biopsy apparatus 10 will now be described. Apparatus 10 is compatible with various guidance systems for diagnostic biopsies and provides interchangeability with such guidance systems with minimum or no modification. This versatility is due in part to its novel configuration and reduction in overall length of housing 12 due to the removable firing module 16 being a separate element of the system.

As shown in FIG. 4, cover 26 is manipulated to an open position. As shown in FIG. 3, outer latch 36 is in a counter-clockwise most position and inner latch 38 in a clockwise most position for receipt of foot 32 of H-latch 30. Wheel knob 40 is in the "twelve o'clock" position for proper orientation and positioning of knife carriage 410 and trocar carriage 420 for receipt and supportive engagement of knife tube 64 and vacuum tube 76, respectively, of insertion unit 14 within carriage housing 12. Pin 230 on inner latch 33 maintains wheel knob 40 in the "twelve o'clock" position and is fixedly mounted to inner latch 38.

As shown in FIGS. 3B and 3C, rear wheel knob 54 and knob lock 50 also function to maintain positioning of knife carriage 410 and trocar carriage 420 for receipt and supportive engagement of insertion unit 14. Wheel knob 50 and rear wheel knob 54 cooperate through shaft 56.

Insertion unit 14 is installed within carriage housing 12. Carriage strip 60 is removed from insertion unit 14 and the components are snapped into carriage housing 12. Cover 26 is closed. Wheel knob 40 and rear wheel knob 54 may be slid rearward and disengaged from latch assembly 34 and knob lock 50, respectively. Latch assembly 34 engages foot 32 to maintain cover 26 in a closed position and support of insertion unit 14 by carriage housing 12.

Apparatus 10 is now installed on an imaging guidance system, for example, stereotactic guidance system (not shown). Firing module 16 is slidably inserted within carriage housing 12. Clock wheel knob 40 is slid back, preferably, by approximately a distance of 0.94 inches so that it contacts ram 190 which will be projected to engagingly contact trocar carriage 420 for piercing a lesion of a patient. Cocking arm 210 is manipulated to cock ram 190 of firing module 16 into a firing ready position.

Firing release assembly 300 is depressed so that motion of ram 190 is permitted. Wheel knob 40 and rear wheel knob 54 are slid rearward to a contacting relation with ram 190.

The stereotactic guidance system is adjusted so that tip portion 62 of insertion unit 14 is adjacent a suspect lesion (not shown) for diagnostic treatment. Trigger button 208 is depressed forcing ram 190 to impart its kinetic energy on trocar carriage 420 engage insertion unit 14, thereby piercing the lesion. Preferably, ram 190 drives only trocar carriage 420 forward thereby minimizing the amount of mass acted upon by ram 190 and maximizing the force imparted on vacuum tube 76.

Figure 17:
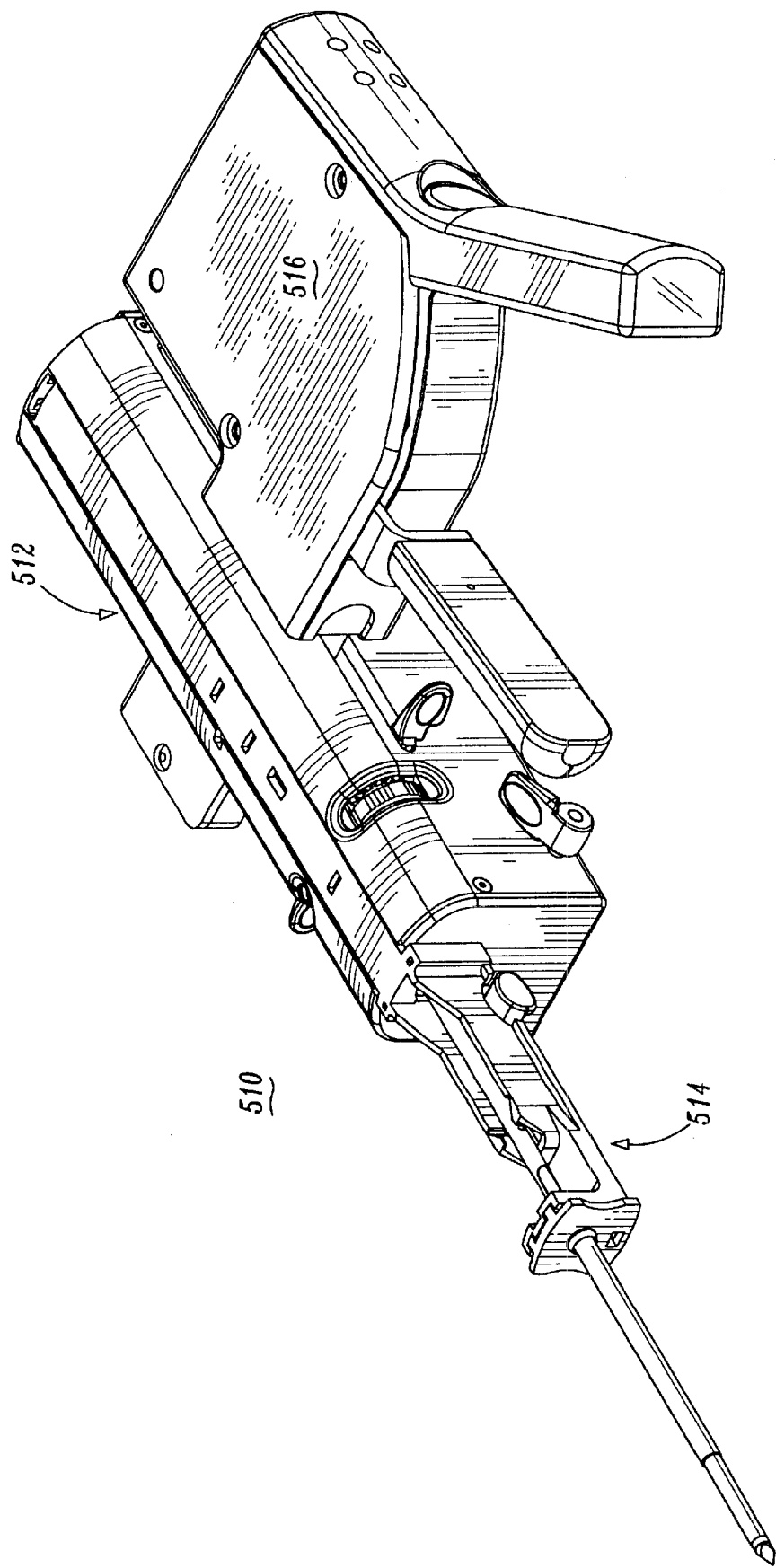
FIG. 17 is a perspective view of an alternative embodiment of a biopsy system constructed in accordance with the present disclosure.
Figure 18:
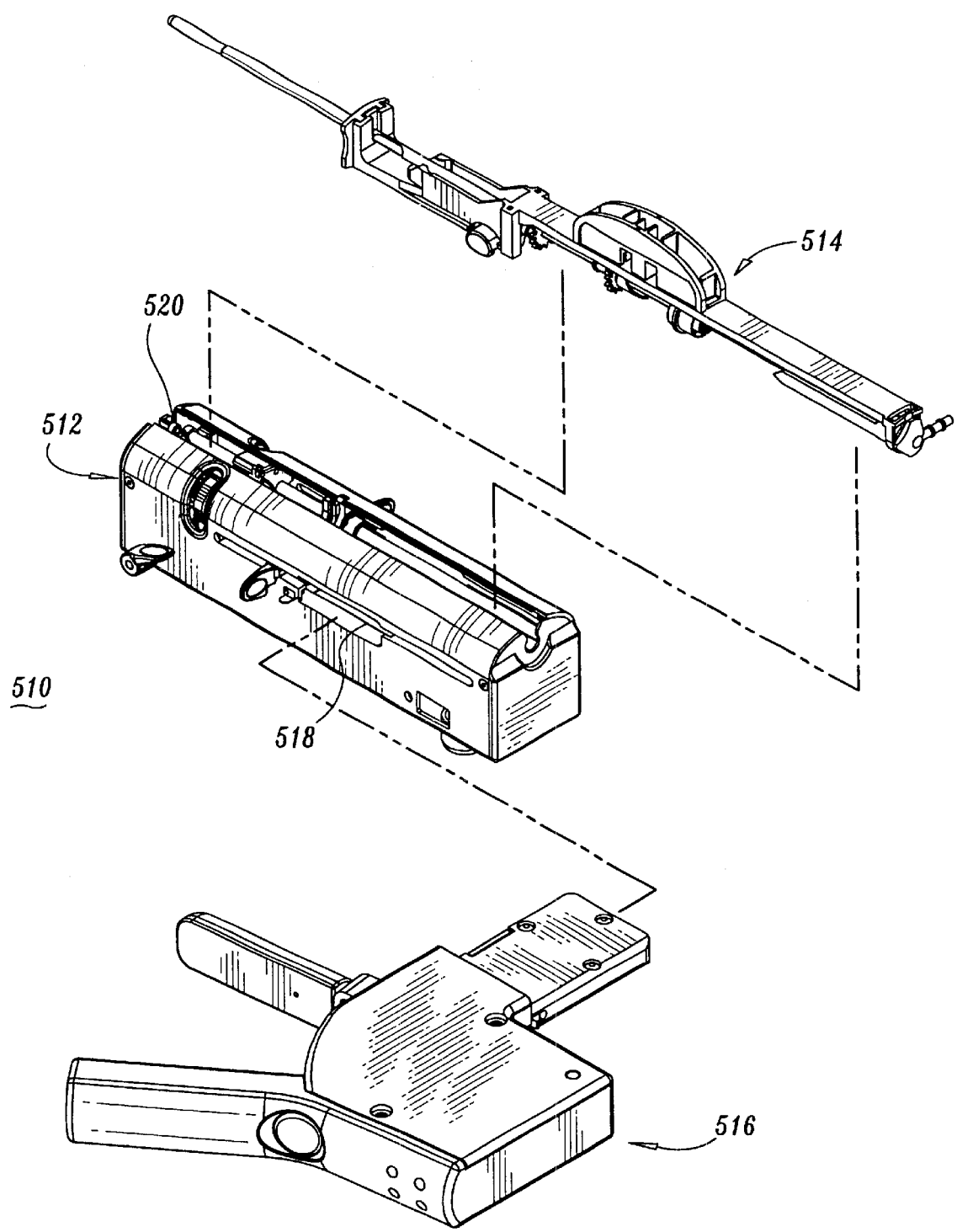
FIG. 18 is a perspective view with parts separated of the biopsy system shown in FIG. 17.

Referring to FIGS. 17 and 18, an alternate embodiment of a biopsy system shown generally as biopsy system 510, for insertion and retrieval of tissue such as, for example, breast biopsy specimens or samples, is disclosed. Biopsy system 510 includes a housing 512 and a biopsy instrument, such as, insertion unit 514. Insertion unit 514 is operatively associated with housing 512 and configured and dimensioned to remove multiple tissue samples from a patient with a single percutaneous insertion of the whole instrument.

A firing module 516 is detachably engageable with housing 512 and operatively associated with insertion unit 514 to facilitate selective rapid advancement of at least a portion of the biopsy instrument toward a targeted location with the patient. Firing module 516 is laterally received within a cavity 518 defined by housing 512 for operative association with insertion unit 514. One of the advantages of the disclosed biopsy system is the facilitation for an operator to extract multiple samples of suspect tissue without withdrawing the entire system from the patient. Further, the system advantageously permits sampling from various radial orientations relative to the biopsy instrument. This results in minimal scarring and outpatient conditions that permit the patient to resume normal activities immediately. Biopsy system 510 may cooperate with a prone table set up, an upright table set up or other diagnostic/treatment apparatus configurations.

Housing 512 extends axially from a proximal end to a distal end of system 510 and defines a cavity 520 for support of insertion unit 514. Housing 512 includes a motorized drive unit and system controls. An example of a drive unit and system controls is disclosed in U.S. Provisional Application Serial No. 60/078,748, described above.

Figure 19:
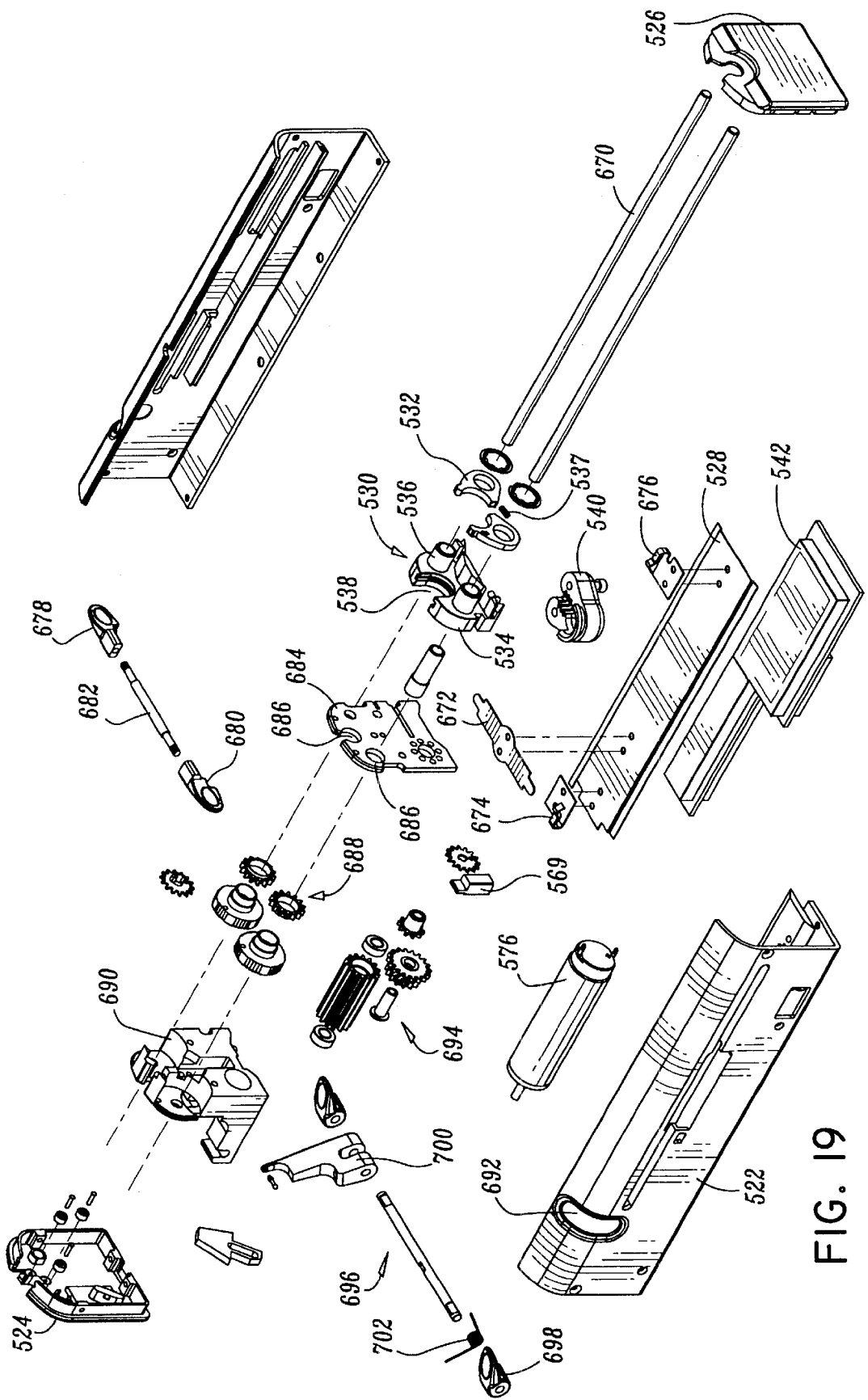
FIG. 19 is a perspective view with parts separated of one embodiment of a housing shown in FIG. 17 and components of the biopsy system disposed therein.

Referring to FIG. 19, biopsy system 510 includes several operational components and mechanisms disposed within housing 512. Housing 512 includes side covers 522, a front cover 524, a rear cover 526 and a base plate 528 for enclosing the various components.

A carriage 530 is slidably disposed within housing 512 and is configured to releasably retain at least a portion of insertion unit 514 within housing 512. Carriage 530 is a retaining mechanism with an over center arrangement configured to retain insertion unit 514 in proper position after actuation of firing module 516. Retainers 532 are mounted to a drive sled 534 and rotate about bushings 536. A spring 537 facilitates resilient motion of retainers 532 about bushings 536.

Figure 20:
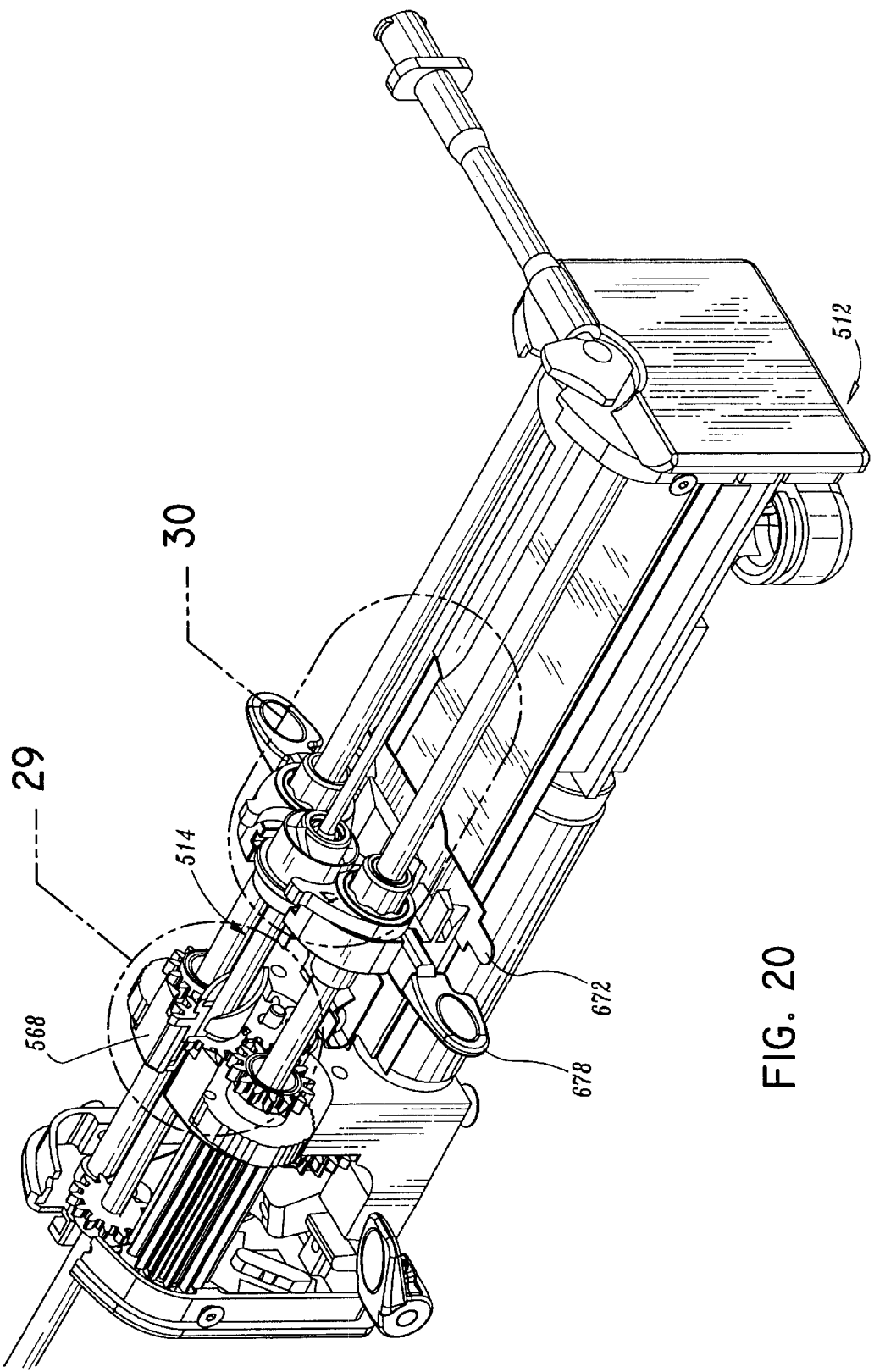
FIG. 20 is an enlarged perspective view showing one embodiment of an indexing assembly of the biopsy system of FIG. 17.

Referring to FIGS. 19 and 20, drive sled 534 is supported within housing 512 by carriage rails 670. Carriage rails 670 are attached to rear cover 526 and are received by bushings 536. A lockout 672 is attached to a bottom surface of carriage 530. Lockout 672 cooperates with a distal detent 674 and a proximal detent 676 providing movable limits of carriage 530. A tissue basket retract slide 678 is mounted to carriage 530 for manipulation thereof. Tissue basket retract slide 678 includes levers 680 attached by a bar 682. A stop 684 prevents motion of carriage 530 at a distal most position. Stop 684 defines cavities 686 for receipt of portions of insertion unit 514.

Insertion unit 514 is releasably received within a cavity 538 of drive sled 534 for releasable receipt within housing 512. Upon receipt within cavity 538, retainers 532 are caused to retain insertion unit 514 in position. Upon actuation of firing module 516, retainers 532 allow motion of insertion unit 514 therein due to firing while maintaining proper positioning.

An optical sensor 540 is disposed adjacent a portion of biopsy instrument 514 (such as, for example, a tubular knife member, described in greater detail below). Optical sensor 540 is oriented to detect a marker (not shown) disposed on insertion unit 514 to determine orientation of the insertion unit (such as a lateral opening in the tubular knife member) discussed below in detail with regard to FIG. 39. Optical sensor 540 includes the required electronics and hardware known to one skilled in the art for sensing position and determining orientation such as, for example, a programmable logic control circuitry generally designated as 542. The details of such circuitry will be addressed later herein in detail with reference to FIG. 35.

Figure 21:
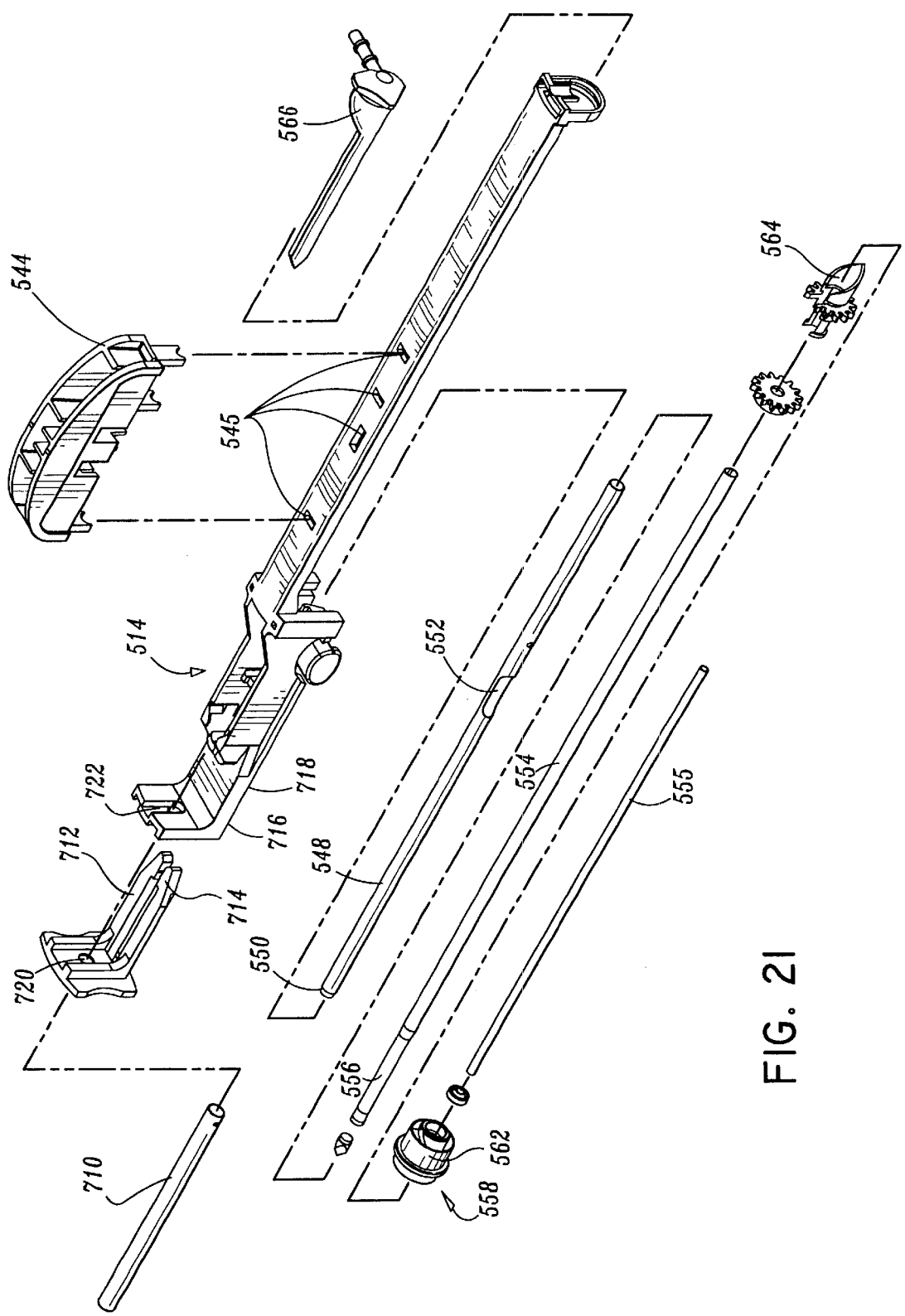
FIG. 21 is a perspective view with parts separated of a biopsy instrument for the embodiment shown in FIG. 17 and an indexing assembly.

Referring to FIG. 20, insertion unit 514 is supported within housing 512. Insertion unit 514 includes, as shown in FIG. 21, a release strip, such as, for example, calibrator 544 for maintaining the components of insertion unit 514 in proper relative axial and radial orientation for loading with housing 512. Calibrator 544 is received within openings 545 formed with insertion unit 514.

Figure 22:
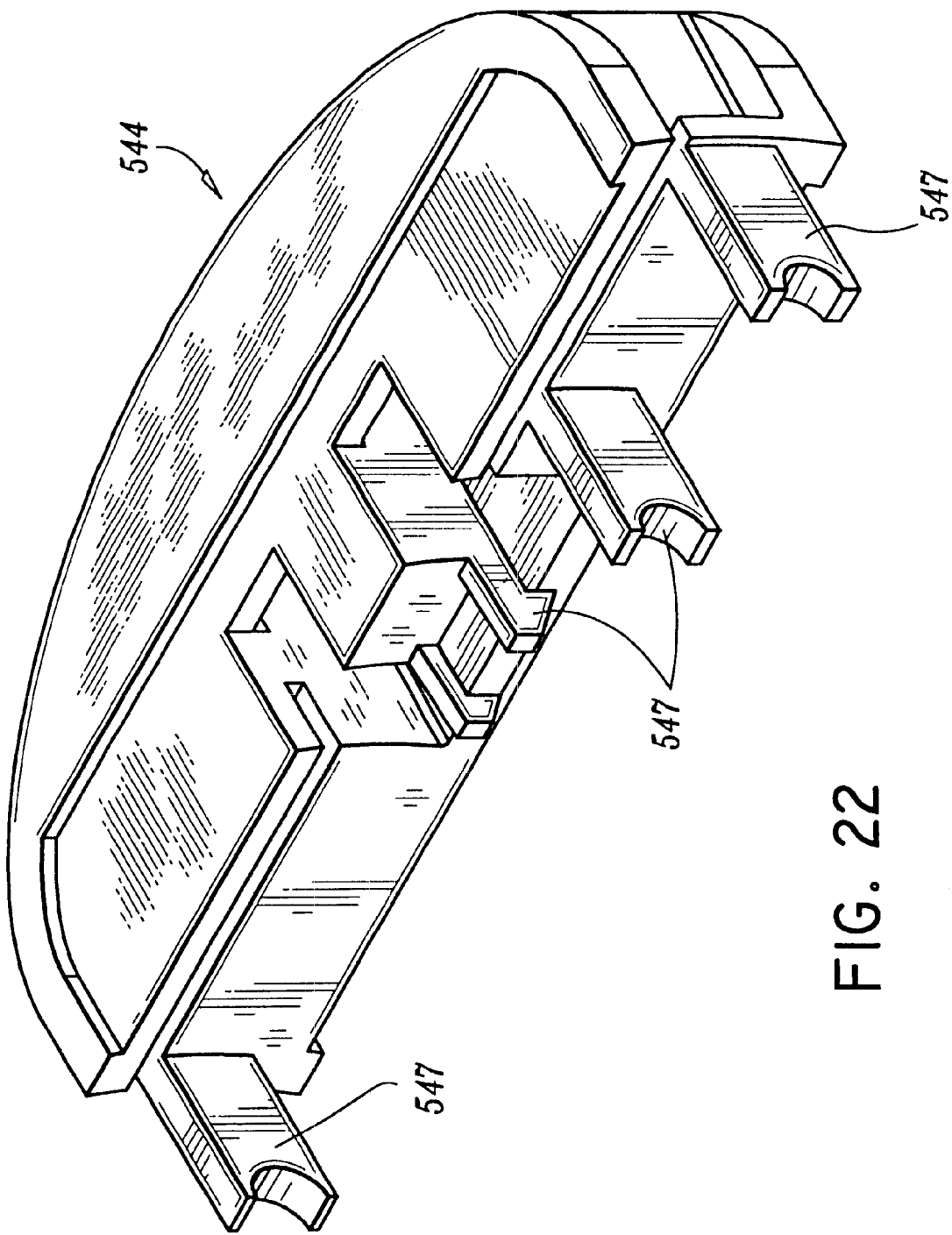
FIG. 22 is an enlarged perspective view of a calibrator for the biopsy instrument shown in FIG. 21.
Figure 23:
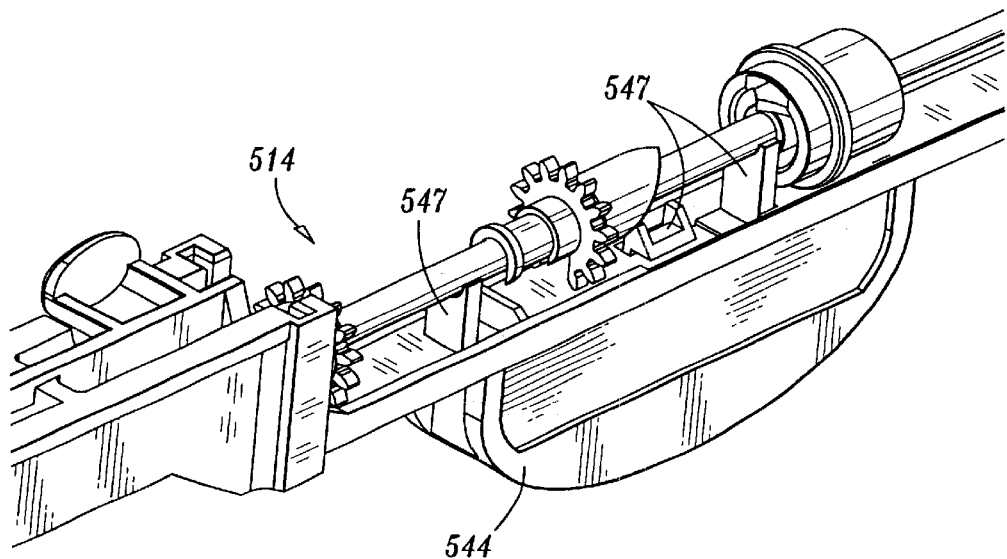
FIG. 23 is an enlarged partial perspective view of the interaction of the calibrator with the biopsy instrument.
Figure 24:
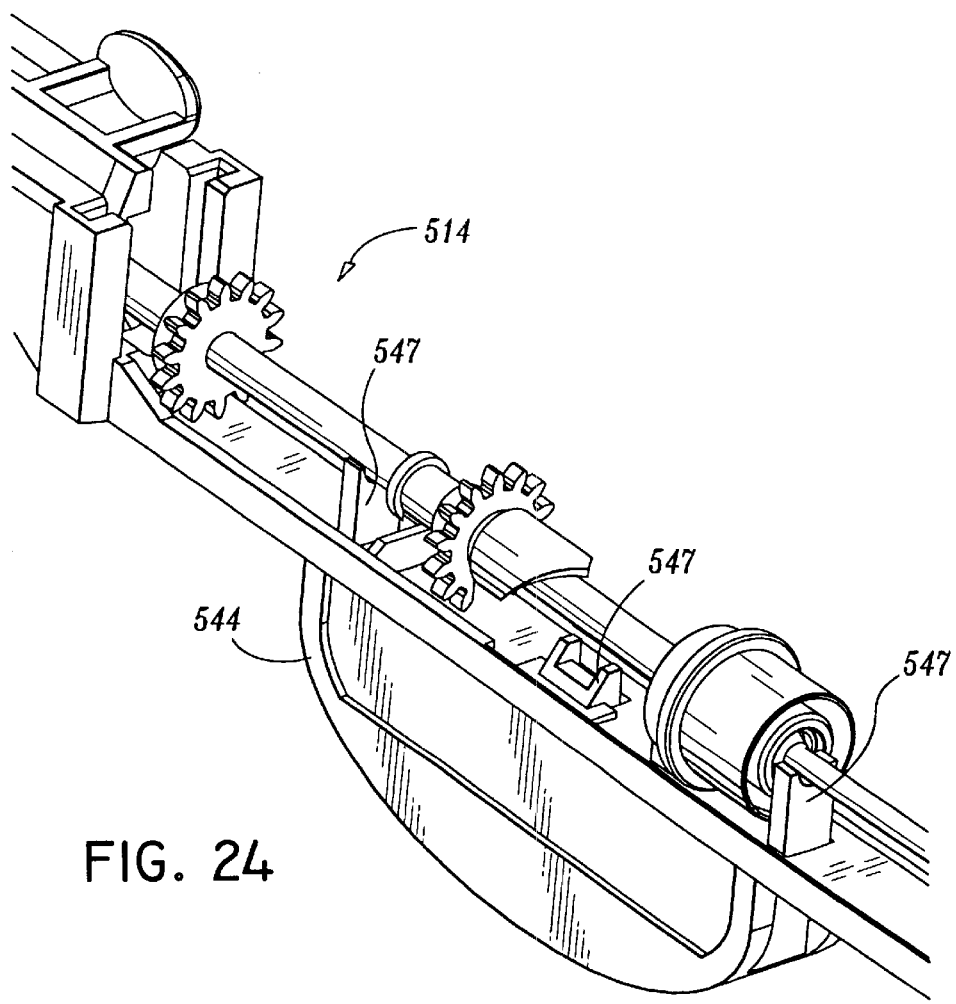
FIG. 24 is an enlarged partial perspective view of the reverse side of the view shown in FIG. 23.

Referring to FIG. 22, calibrator 544 includes pegs 547 for engaging insertion unit 514. Referring to FIGS. 23 and 24, pegs 547 engage portions of insertion unit 514 (such as the knife tube and vacuum tube, discussed below) so that insertion unit 514 may be positioned within housing 512 in a proper orientation, such as, for example, so that a tissue basket of the insertion unit is positioned in the "12 o'clock" position so that insertion unit 514 is properly calibrated in conjunction with the alignment of system 510. This facilitates cooperation so that, for example, the components of insertion unit 514 can be snapped into housing 512, as will be described below. Calibrator 544 orients insertion unit 514 so that a tissue basket, described below, is also in a "twelve o'clock" position. Insertion unit 514 cannot be loaded into housing 512 unless the tissue basket is in the "twelve o'clock" position. This advantageously prevents misalignment of the components and incorrect positioning of the tissue basket. Insertion unit 514 is a single use loading unit and contemplated to be interchangeable with different housings.

Referring to FIG. 21, insertion unit 514 includes a series of concentrically disposed tubular members including a tubular knife member, such as, for example, knife tube 548, similar to that described with regard to FIGS. 1–17. Knife tube 548 has a beveled angular cutting surface 550 and a lateral opening formed therethrough, such as, for example, laterally facing tissue discharge port 552. Actuation of knife tube 548 and connection to a vacuum source is described above.

Insertion unit 514 also includes a first tubular member, such as, for example, trocar 554, similar to vacuum tube 76, described with regard to FIGS. 1–17, and coaxially disposed within knife tube 548. A tissue basket 556 is formed adjacent to the distal end of trocar 554 and is configured and dimensioned similarly to that described with regard to FIGS. 1–17. A vacuum line 555 is positioned in fluid communication with the lumen of trocar 554. Actuation for retrieval of samples and connection to a vacuum source is also similarly described below.

A radiolucent outer tube 710 is attached to a sliding clip 712 which provides removable attachment to insertion unit 514 at a distal end thereof. Outer tube 710 is radiolucent so that it may be left at the tissue sampling cite for imaging of the suspect tissue without the presence of the radiopaque knife tube 548 and trocar 554. Outer tube 710 is, preferably, provided with at least one radiopaque marking such as a peripheral line to indicate the longitudinal spacing of the sampling site in order to provide the user with an indication of the tissue sampling area.

Sliding clip 712 is provided with a pair of deflectable legs 714 which fit within parallel receiving slots 716 formed on the underside of insertion unit 714. A pair of camming surfaces 718 are formed along a wall portion on the underside of insertion unit 514. Camming surfaces 718 act as temporary stops which resist longitudinal movement of sliding clip 712. Sliding clip 712 includes a cavity 720 for alignment and support of outer tube 710 therein. A cavity 722 of insertion unit 514 also aligns and supports outer tube 710.

Upon complete distal movement of sliding clip 712, the distal end of outer tube 710 is substantially aligned with the distal end portion of the location of tissue basket 556 at insertion in the target tissue mass thus providing a marker for the location of the tissue sampling site upon removal of apparatus 510 from the suspect tissue region.

Biopsy system 510 includes an indexing assembly 558 operatively engageable with insertion unit 514 for selective orientation of tissue basket 556. Indexing assembly 558 includes a camming assembly disposed in cooperation with trocar 554 and an indexing gear assembly 688 that facilitates indexing movement of indexing assembly 558. The camming assembly allows apparatus 510 to retrieve samples having tissue basket 556 at different radial orientations that can advantageously recall the position of the prior sample taken. This arrangement provides an auto-indexing feature for recalling position of the prior sample and resetting for proper position for subsequent sample removal which advantageously increases efficiency of the biopsy sample procedure.

Figure 25:
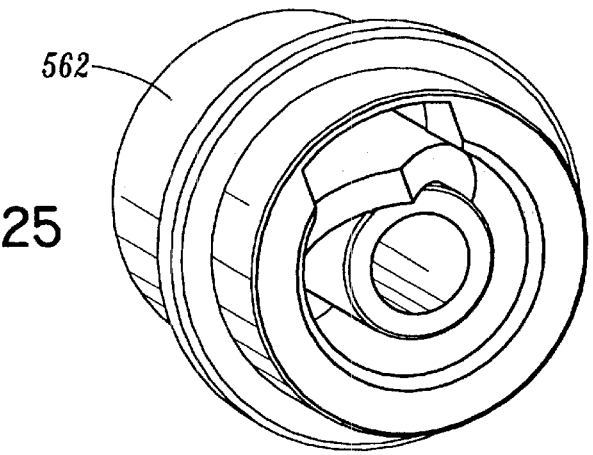
FIG. 25 is an enlarged perspective view of a tissue basket face cam of the biopsy instrument shown in FIG. 21.
Figure 26:
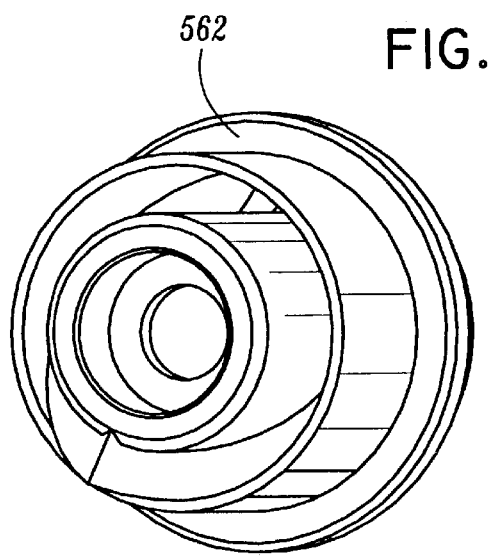
FIG. 26 is an enlarged perspective view of the reverse side of the view shown in FIG. 25.
Figure 27:
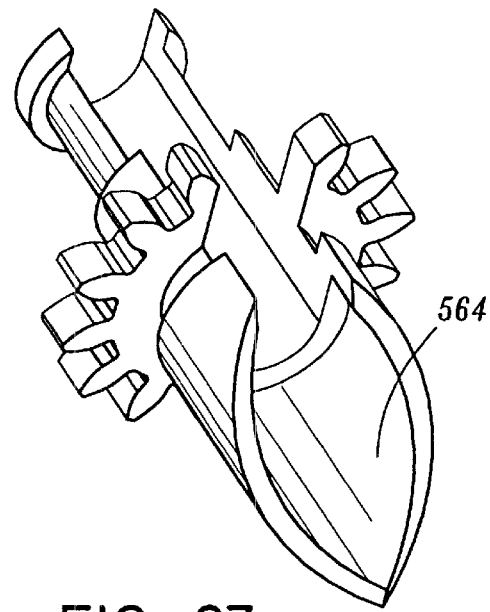
FIG. 27 is an enlarged perspective view of a position cam of the biopsy instrument shown in FIG. 21.
Figure 28:
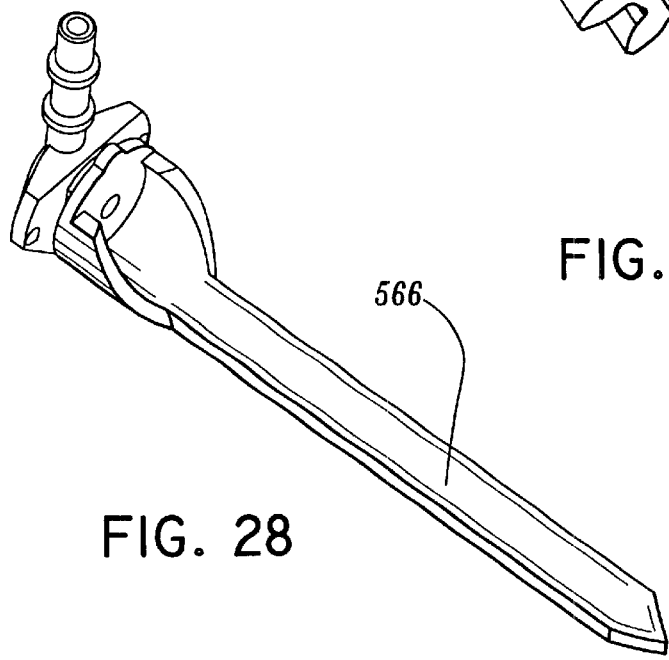
FIG. 28 is an enlarged perspective view of a removal cam of the biopsy instrument shown in FIG. 21.

As shown in FIG. 21, in conjunction with FIGS. 25–28, indexing assembly 558 includes a first cam member 562, FIGS. 25 and 26, for mounting to trocar 554. First cam member 562 is configured to cooperate with a second cam member 564, FIG. 27, disposed within housing 512 to orient tissue basket 556 to a predetermined orientation for obtaining a discrete tissue sample. First cam member 562 is further configured to cooperate with a third cam member 566, FIG. 28, disposed within housing 512 to orient tissue basket 556 to a predetermined orientation for removal of a tissue sample.

Figure 29:
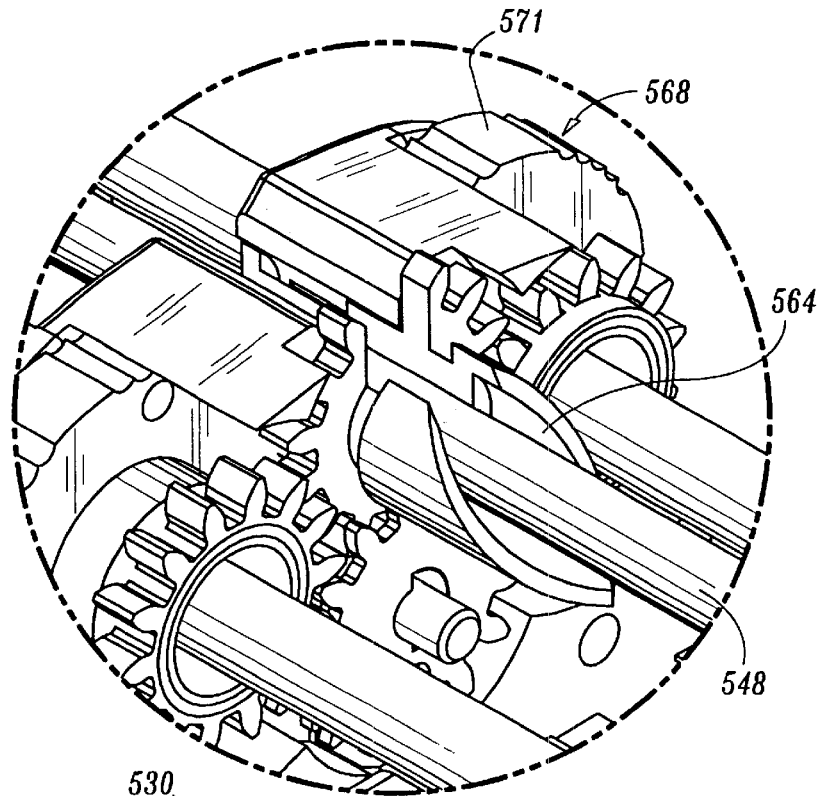
FIG. 29 is an enlarged cut-away section of the indicated area of detail shown in FIG. 20.

Referring to FIG. 29, indexing assembly 558 includes a manual gearing assembly 563, FIG. 20, configured to selectively orient tissue basket 556. Manual gearing assembly 568 includes a pair of thumb wheels 571 facilitating manual orientation of tissue basket 556 and proper alignment within housing 512. Second cam member 564 is oriented with manual gear assembly 568 for indexing tissue basket 556 to the desired radial orientation for sample retrieval, sample removal or assembly of system 510. Referring temporarily to FIG. 19, thumbwheels 571 are supported within housing 512 by an index carriage 690. Side covers 522 define apertures 692 for exposing at least a portion of thumbwheels 571 for manipulation thereof.

Figure 30:
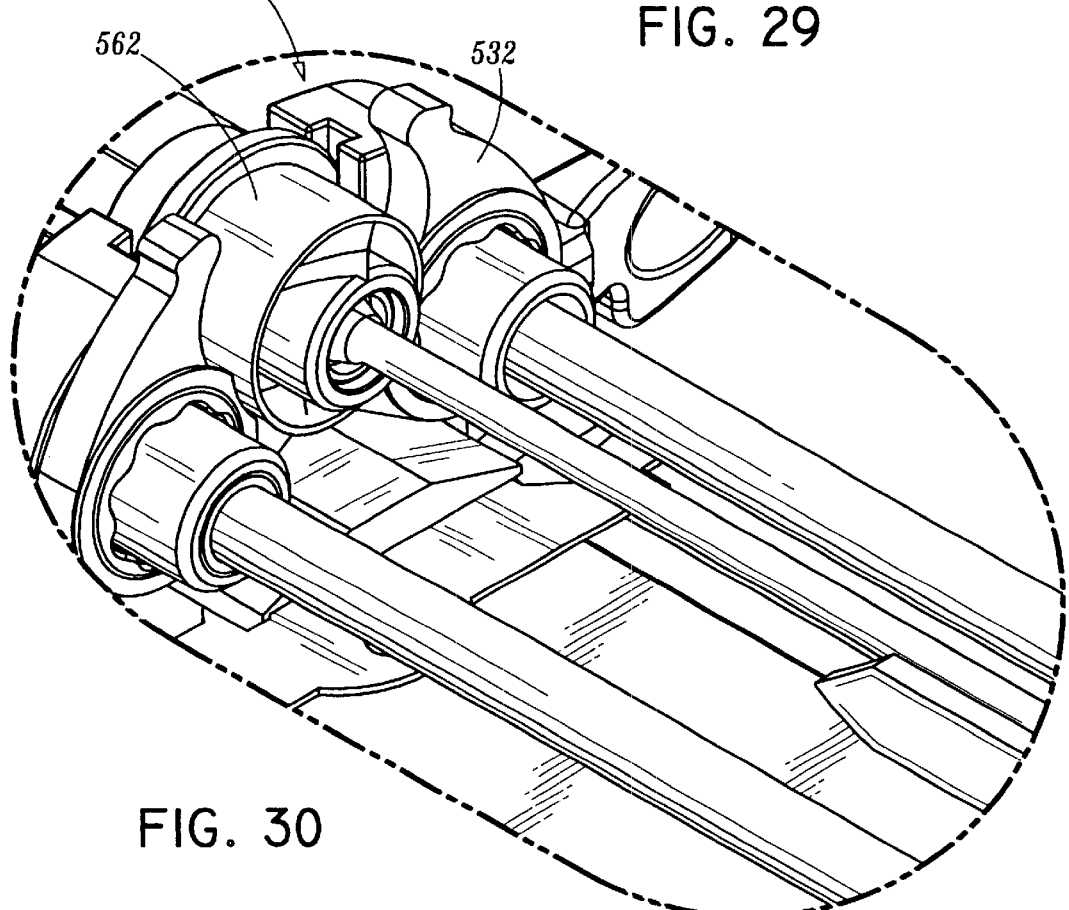
FIG. 30 is an enlarged cut-away section of the indicated area of detail shown in FIG. 20.

With continued reference to FIG. 29, system 510 is assembled by manipulating thumbwheels 571 of manual gear assembly 568 so that the second cam member 564 is in the "twelve o'clock" position. Knife tube 548 is received by second cam member 564. Correspondingly, as shown in FIG. 30, first cam member 562 is received by carriage 530 whereby retainers 532 retain first cam member 562 and insertion unit 514 therein.

Referring to FIG. 31, tissue retrieval of a discrete tissue sample is facilitated by system 510 having second cam member 564 oriented in the "twelve o'clock" position with trocar 554 therein. First cam member 562 is mounted to trocar 554. Referring to FIG. 32, trocar 554 and first cam member 562 are driven forward, shown by arrow "A", so that first cam member 562 cooperates with second cam member 564 for indexing capability. As first cam member 562 cooperates with second cam member 564, first cam member 562 is caused to rotate, as shown by arrow "B", for proper alignment of tissue basket 556, for retrieval of a discrete tissue sample.

Thumbwheels 571 (FIG. 29) of manual gearing assembly 568 are manipulated to orient the tissue basket 556 adjacent a tissue sampling site. An index stop 569 (FIG. 19) cooperates with gearing of indexing assembly 558 facilitating "2-hour" increments about and relative to trocar 554 for retrieving tissue samples. Upon retraction of trocar 554 with system 510, to remove a tissue sample, the orientation of second cam member 564 is not affected, advantageously providing a position memory of where the previous sample was retrieved.

Figure 33:
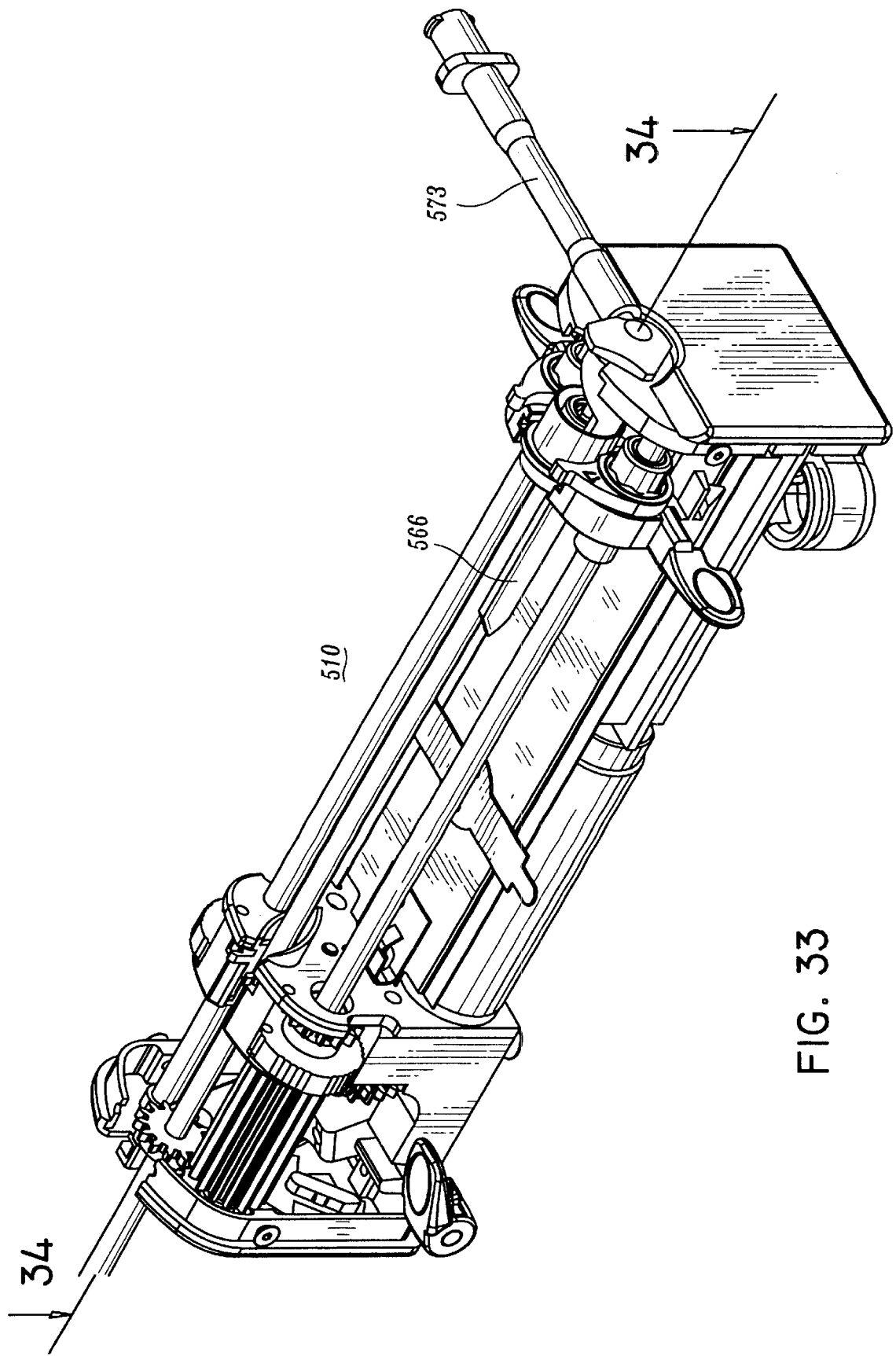
FIG. 33 is an enlarged partial perspective view of the biopsy system shown in FIG. 17 with the housing cover components removed to illustrate the various functional assemblies of the biopsy system.

Referring to FIGS. 33–35, removal of the tissue sample is facilitated by. system 510 employing third cam member 566. Trocar 554 and first cam member 562 are driven in a proximal direction, shown by arrow "C", so that first cam member 562 cooperates with third cam member 566. As first cam member 562 cooperates with third cam member 566, first cam member 562 is caused to rotate, as shown by arrow "D", orienting tissue basket 556 to one side or the other.

Advantageously, because the operator will always orient the vacuum elbow 573 to point away from the side on which they are positioned, first cam member 566 will orient tissue basket 556 opposite the connection to the vacuum source (discussed below with regard to FIG. 8), as shown in FIG. 33.

Figure 36:
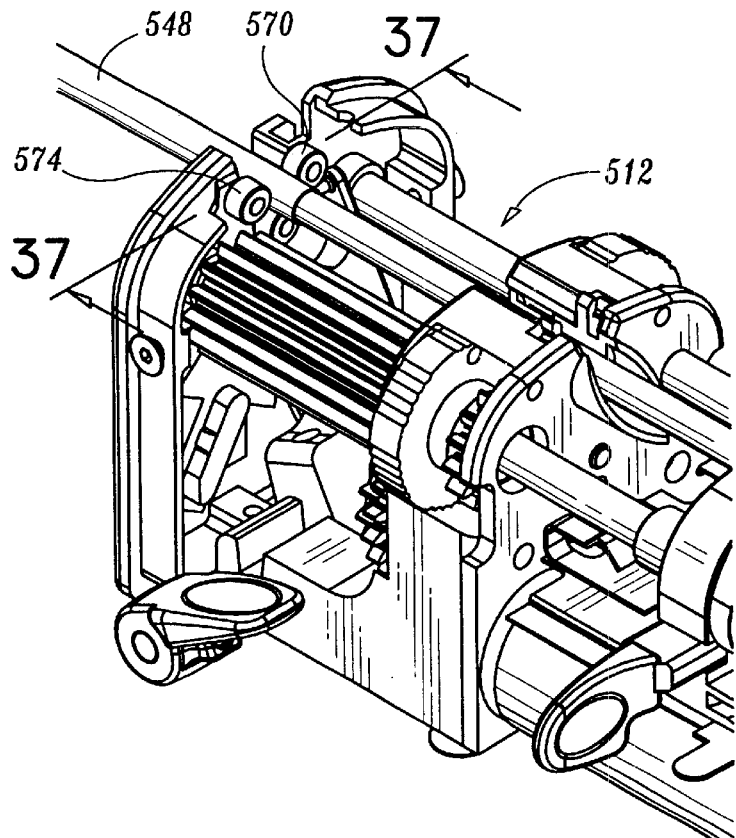
FIG. 36 is an enlarged perspective view of the various components disposed near the distal end of the biopsy system housing shown in FIG. 17.
Figure 37:
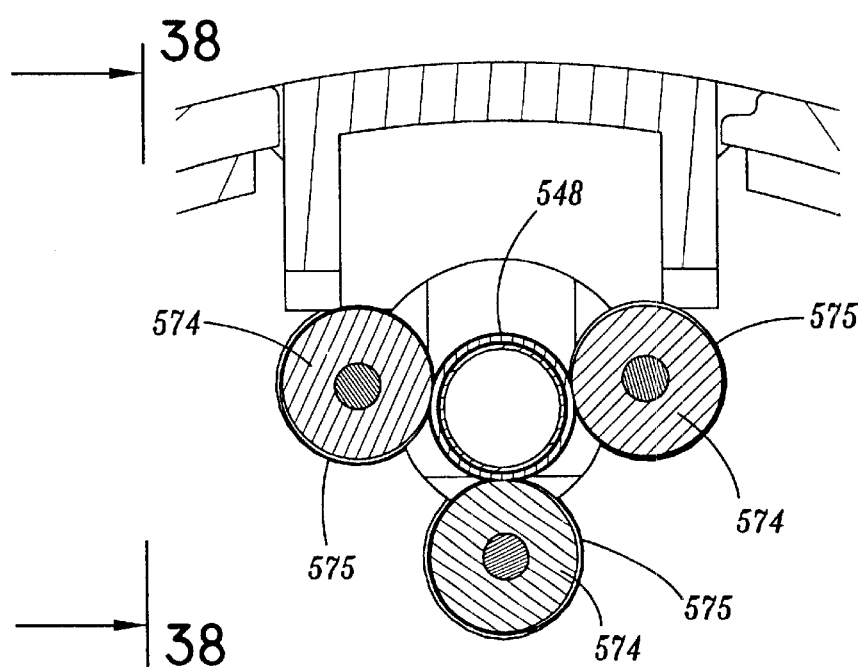
FIG. 37 is a cross-sectional view of one embodiment of a linear advancement control assembly taken along section line 37—37 of FIG. 36.
Figure 38:
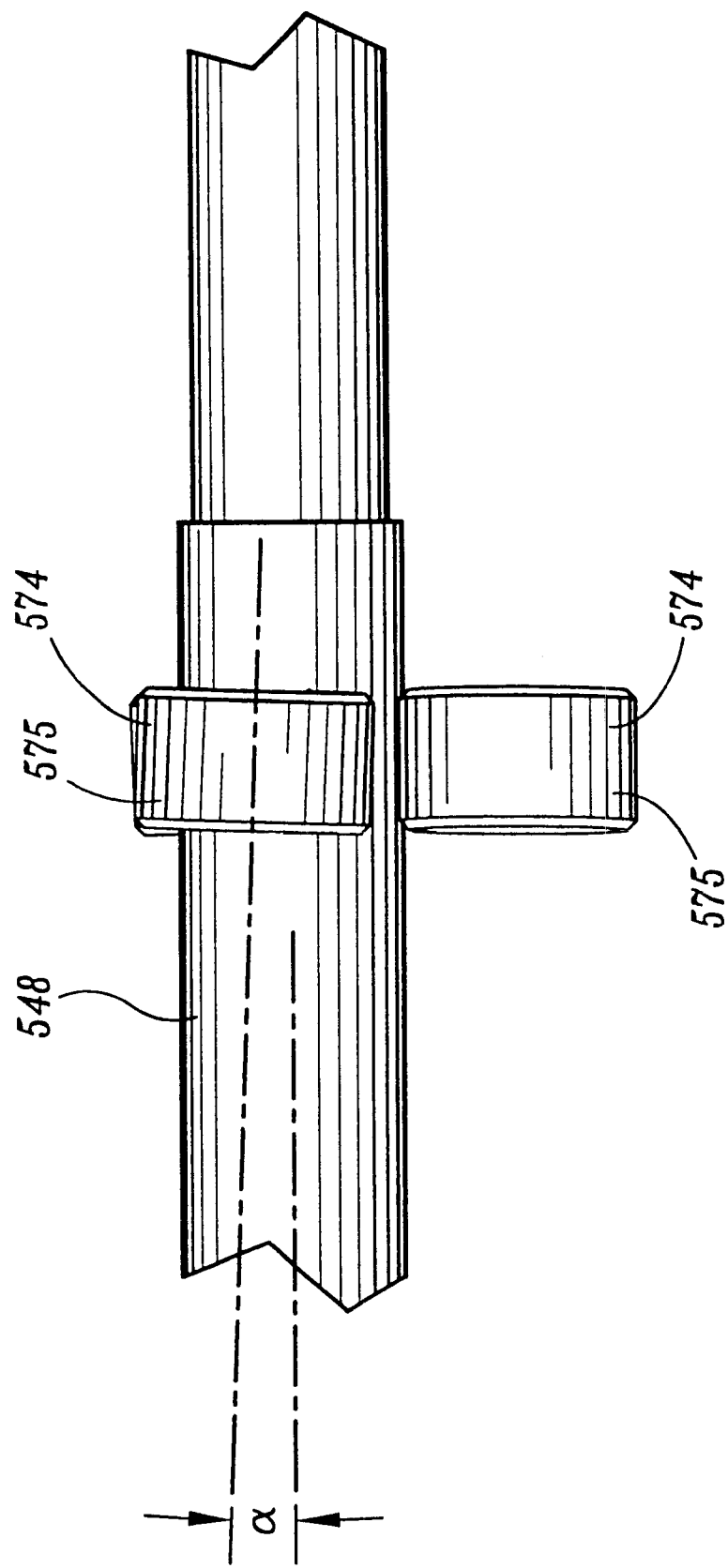
FIG. 38 is a partial view taken along section line 38—38 of FIG. 37.

Referring to FIGS. 36–38, biopsy system 510 includes a linear advancement control assembly 570 disposed within housing 512 and configured to effect linear actuation of knife tube 548. Assembly 570 includes bearings 574 mounted with housing 512 and configured to effect linear movement of knife tube 548. Preferably, three bearings 574 are oriented and configured such that contact surfaces 575 of bearings 574 form a partially helical thread configuration which effects axial translation of knife tube 548 upon rotation thereof. Specifically, as shown in FIG. 38, each of bearings 574 is tilted at an angle a offset from the longitudinal axis. One particularly effective angle is approximately 2°.

Typically these bearings are spaced 120° apart. However, for purposes of the presently disclosed biopsy system, the bearing spacing has been advantageously modified. Referring to FIG. 37, bearings 574 are oriented relative to each other such that tubular knife member 548 may be snap fit in between two of bearings 574. Bearings 574 are concentrically disposed about knife tube 548 and are in contact therewith.

Rotation of knife tube 548 is preferrably effected by electric motor 576 (FIG. 19). A drive gear train 694 is operatively associated with motor 576 to effect rotation of knife tube 548. Bearings 574 convert rotation of knife tube 548 into axial translation. This auto-feed feature of biopsy system 510 advantageously allows electric motor 576 to set the knife feed rate or advance speed.

If resilient tissue is encountered, the helical thread formed by bearings 574 causes knife tube 548 to slip, slowing its forward advance while continuing to rotate until knife tube 548 cuts through the tissue. As knife tube 548 is advanced, assembly 570 slows feed rate so that knife tube 548 completely cuts the desired tissue sample. Assembly 570 eliminates the need for complicated mechanisms to advance knife tube 548 which is further enhanced by the snap-in feature, discussed above.

Referring temporarily to FIG. 19, a knife tube retract mechanism 696 engages drive gear train 694 for retracting knife tube 548 from a tissue sample location in between bearings 574. Knife tube retract mechanism 696 includes levers 698 for manipulation thereof. A cam 700 is mounted to mechanism 696 for engaging gear train 694. A torsion spring 702 biases mechanism 696 between its movable limits.

In operation, such as, for example, in a breast biopsy procedure discussed above, insertion unit 514 is assembled with the remaining components of biopsy system 510. Calibrator 544 is prepackaged and assembled with insertion unit 514 for maintaining proper orientation of the components of insertion unit 514, as previously discussed with regard to FIGS. 20–24. Upon operative connection of insertion unit 514 to housing 512, calibrator 544 is removed.

Insertion unit 514 engages system 510 whereby portions of the insertion unit are received or snapped into position. As discussed above, knife tube 548 is received by second cam member 564 (FIG. 29). First cam member 562, mounted to trocar 554, is received by carriage 530 (FIG. 30) and knife tube 548 is snapped in between bearings 574. Biopsy instrument 514 is advantageously releasably retained by system 510.

Biopsy system 510 is installed on an imaging guidance system, for example, a stereotactic guidance system similar to that discussed above. Firing module 516 is detachably engaged with cavity 518 of housing 512 for operative association with biopsy instrument 514. Firing module 516 may be manipulated to cock firing module 516 for firing of biopsy system 510, similar to that discussed with regards to FIGS. 1–17. Briefly, upon firing of firing module 516, hammer 517 (FIG. 31) is thrust against carriage 530 thereby rapidly thrusting trocar 554 into the selected target tissue region. Alternatively, firing module may be pre-cocked before installation in biopsy system 510.

Indexing assembly 558 engages insertion unit 514 for selective orientation of tissue basket 556, similar to that described with regard to FIGS. 29–35. First cam member 562 mounted to trocar 554 is driven in a distal direction for cooperating with second cam member 564 for advantageously indexing the orientation of tissue basket 556. Manual gearing assembly 568 is manipulated to position tissue basket 556 at a desired orientation where a suspect lesion or desired tissue sample is located (not shown).

Knife tube 548 is actuated whereby the programmable logic controls (described in greater detail further herein) start electric motor 576 (FIG. 19) which causes rotation of knife tube 548. Linear advancement control assembly 570 controls actuation of knife tube 548 including feed rate for severing a discrete tissue sample as discussed with regard to FIGS. 36–38. As previously noted, in the event that resilient tissue is encountered, knife tube 548 is caused to slip axially, reducing feed rate until the desired tissue is removed. First cam member 562 is driven in a proximal direction for cooperating with third cam member 566 for removal of the tissue sample, as discussed with regard to FIGS. 33–35. Advantageously, first cam member 562 is driven in a distal direction for cooperation with second cam member 564, so that orientation of tissue basket 556 for the previous sample position is recalled. A subsequent discrete sample can be retrieved at the same position or another selected position knowing where the previous tissue was sampled from.

Figure 39:
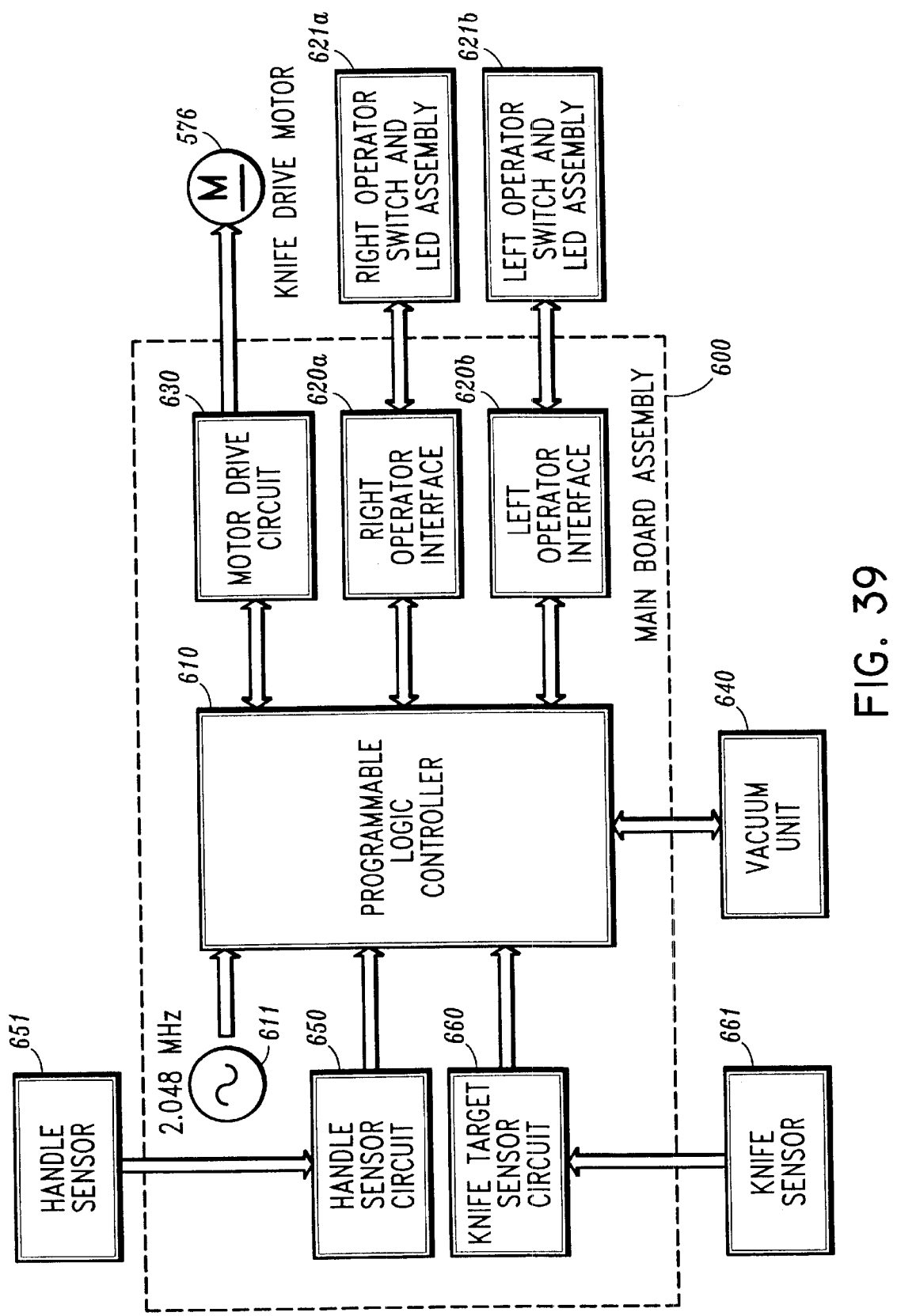
FIG. 39 is a block diagram of a logic controller of the biopsy system.

Referring to FIG. 39, biopsy system 510 includes a programmable logic control system. In operation, once insertion unit 514 is positioned and ready to fire, the user pushes the firing button on firing module 516, similar to that discussed above. The hammer of firing module 516 impacts trocar carriage 530 and rapidly moves it distally, thereby forcing trocar 554 along with tissue basket 556 into the targeted tissue area. To initiate the cutting process, the user pushes one of the enable switches 621 a or 621b (located on either right side or left side of housing 512 depending on how biopsy system 510 has been set up for the given procedure). That action sends a signal through the interface circuit 620a or 620b which then sends a process signal into the programmable logic controller ("PLC") 610. The logic state is thereby changed to put it into an enabled mode which provides an enable signal to the motor driver 630 thus enabling the motor driver 630 to control motor 576. The enable switches are on-off type alternate action switches, i.e., pushed once to turn on and pushed again to turn off, correspondingly turning on the enabled LED indicator.

The knife control handle is pushed down which sends a signal to the knife optical sensor 661 which detects the fact that the knife control handle is back and sends a signal into PLC 610 which starts a logic sequence that turns off a pinch valve allowing vacuum to flow. When the knife control handle is put on, the vacuum starts, when the knife control handle releases, there is a slight delay, for example, one second, before motor 576 starts which begins advancing the motion of knife tube 548. It will also turn on the automatic function LED 621a or 621b providing the user with a visual indication that the automatic function mode is enabled.

When the operator lets go of the knife handle it is then moved forward by a spring that turns off handle sensor 651 and that information is communicated to PLC 610 which starts the automatic sequence by sending a pulse modulated signal to motor 576 which starts motor 576 turning thereby rotating knife tube 548 which advances forward due to the action of bearings 574. The normal operating speed during cutting is approximately 1200–1600 rpm.

As knife tube 548 approaches the distal end of tissue basket 556, there is an optical target provided on knife gear 694 which is detected by knife target optical sensor 661 positioned adjacent the front of the device. When the optical target, for example, a black stripe applied to one half of the gear hub, starts to move in front of knife target sensor 661 as the motor is turning, it starts to turn knife sensor 661 on and off rapidly and this provides a chopped input signal into the system logic which is preprogrammed to detect a certain number of counts in knife sensor 661 within a certain period of time.

As a safety feature, while motor 576 is running, the current is monitored by an over current protector circuit part of motor drive circuit 630. If the current gets too high above an extreme threshold, for example, approximately 0.6 amps, it determines the motor is excessively slowed and the logic will tell motor 576 to alter to full power and maintain the motor on 100 percent of the time instead of a pulse modulation, so as to provide the motor with more power. Also, as the current rises, for example, above 0.9 amps, the motor is automatically shut off.

As a certain number of pulses are detected by the knife target sensor 660, PLC 610 recognizes the pattern that is predetermined for setting the distal limit of knife travel, it delays about 3 seconds to assure the knife travels all the way to the distal end of tissue basket 556 to complete severing of the target tissue. At the end of that 3 second period, the logic goes into a different state and it drops motor 631 down to a slow speed, for example, between approximately 125 and approximately 208 rpm. At that point the logic searches looking for input from knife target sensor 660 and it uses a feedback system drive circuit 630 to adjust the pulse switch modulation signal going to the control motor 576 in order to achieve a certain speed being measured by the knife target sensor 660. Once the speed of motor 576 is within the acceptable limits, for example, 125–208 rpm, knife target sensor circuit 660 looks for an edge of the stripe on the optical target. The optical target is black on one side and white on the other and as it turns in one direction, knife sensor 661 seeks a black to white edge and then it seeks a white to black edge and stops motor 576 the instant it detects that condition.

The target sensor edge pattern that knife sensor 661 seeks to detect depends upon which user enable switch was pushed. For example, if the operator is standing on the left side of biopsy system 510 and pushes the switch on the left side, one edge pattern sequence occurs and if the operator is on the other side, the other edge pattern sequence occurs. The control circuitry may also incorporate another time delay at this point before the vacuum is automatically turned off.

Motor driver 630 controls the voltage to motor 576. The motor driver 630 includes an overcurrent sensing circuit as previously noted. An oscillator circuit 611 is provided and is used by the logic to produce timing signals for the various sequences. The timing signals stop when knife tube 548 is still in its most distally advanced position. Knife tube 548 is now positioned to pull the tissue out on the indicated side, and the slide 577 (FIG. 34) is pulled back. When the tissue sample is retrieved, the process can be repeated without having to re-fire trocar 554 to the target site because knife tube 548 stays at the site.

To stop knife tube 548 at any time during advancement, the operator simply pushes one of the enable switches to turn off the enable mode thereby preventing further advancement. At any time during the procedure, pushing the manual vacuum button will open the valve and allow vacuum flow.

It will be understood that various modifications may be made to the illustrative embodiments disclosed herein. Therefore, the above description should not be construed as limiting, but merely as exemplification of preferred embodiments. Those skilled in the art will envision other modifications within the scope and spirit of the present disclosure.

What is claimed is:

1. A biopsy system comprising:
   a housing;
   a biopsy instrument operatively associated with the housing, the biopsy instrument being configured and dimensioned to remove a tissue sample from a patient, wherein the biopsy instrument includes a tissue receiving portion and a tubular member cooperating with the tissue receiving portion, and wherein the biopsy system further includes an indexing assembly being disposed within the housing and including a camming assembly disposed on the tubular member, the indexing assembly being configured to cooperate with the biopsy instrument to selectively orient the tissue receiving portion; and
   a firing module being detachably engageable with the housing and operatively associated with the biopsy instrument to facilitate selective rapid advancement of at least a portion of the biopsy instrument toward a targeted location with the patient.

2. A biopsy system comprising:
   a housing;
   a biopsy instrument operatively associated with the housing, the biopsy instrument being configured and dimensioned to remove a tissue sample from a patient, wherein the biopsy instrument includes a tissue receiving portion and a tubular member cooperating with the tissue receiving portion, and wherein the biopsy system further includes an indexing assembly being disposed within the housing and including a camming assembly having a first cam member mounted on the tubular member, the first cam member being configured to engage a second cam member disposed within housing; the indexing assembly being configured to cooperate with the biopsy instrument to selectively orient the tissue receiving portion; and
   a firing module being detachably engageable with the housing and operatively associated with the biopsy instrument to facilitate selective rapid advancement of at least a portion of the biopsy instrument toward a targeted location with the patient.

3. A biopsy system comprising:
   a housing;
   a biopsy instrument operatively associated with the housing, the biopsy instrument being configured and dimensioned to remove a tissue sample from a patient; wherein the biopsy instrument includes a tubular member having a tissue receiving portion disposed near a distal end thereof, the biopsy instrument further including a tubular knife member coaxially disposed relative to the tubular member and being configured for actuation relative to the tubular member for severing tissue;
   a linear advancement control assembly disposed within the housing and configured to effect linear actuation of the tubular knife member; wherein the linear advancement control assembly includes a plurality of bearings mounted within the housing and being configured to effect linear movement of the tubular knife member; and
   a firing module being detachably engageable with the housing and operatively associated with the biopsy instrument to facilitate selective rapid advancement of at least a portion of the biopsy instrument toward a targeted location with the patient.

4. A biopsy system as recited in claim 3, wherein the plurality of bearings include three bearings oriented relative to each other such that the tubular knife member may be snap fit in between two of the bearings.

5. A biopsy system comprising:
   a housing;
   a biopsy instrument operatively associated with the housing, the biopsy instrument being configured and dimensioned to remove a tissue sample from a patient; wherein the biopsy instrument includes a tubular member having a tissue receiving portion disposed near a distal end thereof, the biopsy instrument further including a tubular knife member coaxially disposed relative to the tubular member and being configured for actuation relative to the tubular member for severing tissue;
   a firing module being detachably engageable with the housing and operatively associated with the biopsy instrument to facilitate selective rapid advancement of at least a portion of the biopsy instrument toward a targeted location with the patient; and
   an optical sensor disposed adjacent a portion of the tubular knife member and being oriented to detect the orientation of a lateral opening formed through the tubular knife member.

6. A biopsy system as recited in claim 1, further comprising a carriage being slidably disposed within the housing and being configured to releasably retain at least a portion of the biopsy instrument within the housing.

7. A biopsy system comprising:
   a housing,
   a biopsy instrument being operatively associated with the housing and including a first tubular member having a tissue basket formed near a distal end thereof, the tissue basket being configured for retrieval of tissue, the biopsy instrument further including a tubular knife member coaxially disposed relative to the first tubular member and being configured for cooperative movement with the first tubular member to sever a tissue sample from a patient;
   an indexing assembly operatively engageable with the biopsy instrument for selective orientation of the tissue basket; and
   a linear advancement control assembly configured to effect linear actuation of the tubular knife member, wherein the linear advancement control assembly includes a plurality of bearings mounted within the housing and being configured to effect linear movement of the tubular knife member, and wherein the plurality of bearings are oriented relative to each other such that the tubular knife member may be snap fit in between two of the bearings.

8. A biopsy system as recited in claim 7, wherein the first tubular member includes a first cam member configured and dimensioned to cooperate with the indexing assembly to facilitate selective orientation of the tissue basket.

9. A biopsy system as recited in claim 8, the first cam member being configured to cooperate with a second cam member being disposed within the housing to orient the tissue basket to a predetermined orientation for obtaining a discrete tissue sample.

10. A biopsy system as recited in claim 8, the first cam member being configured to cooperate with a third cam member disposed within the housing to orient the tissue basket to a predetermined orientation for removal of tissue sample from the tissue basket.

11. A biopsy system as recited in claim 7, wherein the indexing assembly includes a manual gearing assembly configured to selectively orient the tissue basket.

12. A biopsy system comprising:

a housing, a biopsy instrument being operatively associated with the housing and including a first tubular member having a tissue basket formed near a distal end thereof, the tissue basket being configured for retrieval of tissue, the biopsy instrument further including a tubular knife member coaxially disposed relative to the first tubular member and being configured for cooperative movement with the first tubular member to sever a tissue sample from a patient;

an indexing assembly operatively engageable with the biopsy instrument for selective orientation of the tissue basket; and an optical sensor disposed adjacent a portion of the tubular knife member and being orientated to detect the orientation of a lateral opening formed through the tubular knife member.

13. A biopsy system comprising:

a housing;

a biopsy instrument being disposed within the housing and including a first tubular member having a tissue basket disposed near a distal end thereof, the tissue basket being configured for retrieval of tissue, the biopsy instrument further including a tubular knife member coaxially disposed relative to the first tubular member and being configured for actuation relative to the first tubular member to effect severing a discrete tissue sample; and a linear advancement control assembly disposed within the housing and configured to cause actuation of the tubular knife member, wherein the linear advancement control assembly includes a plurality of bearings mounted within the housing and being configured to effect movement of the tubular knife member, and wherein the plurality of bearings include three bearings are oriented relative to each other such that the tubular knife member may be snap fit in between two of the bearings.

14. A biopsy system comprising:

a housing;

a biopsy instrument being disposed within the housing and including a first tubular member having a tissue basket disposed near a distal end thereof, the tissue basket being configured for retrieval of tissue, the biopsy instrument further including a tubular knife member coaxially disposed relative to the first tubular member and being configured for actuation relative to the first tubular member to effect severing a discrete tissue sample; and a linear advancement control assembly disposed within the housing and configured to cause actuation of the tubular knife member, wherein the linear advancement control assembly includes a plurality of bearings mounted within the housing and being configured to effect movement of the tubular knife member, and wherein the plurality of bearings are oriented and configured such that contact surfaces of the respective bearings form a partial helical thread which effects axial translation of the tubular knife member.

15. A biopsy system comprising:

a housing;

a biopsy instrument being disposed within the housing and including a first tubular member having a tissue basket disposed near a distal end thereof, the tissue basket being configured for retrieval of tissue, the biopsy instrument further including a tubular knife member coaxially disposed relative to the first tubular member and being configured for actuation relative to the first tubular member to effect severing a discrete tissue sample;

a linear advancement control assembly disposed within the housing and configured to cause actuation of the tubular knife member;

an indexing assembly being operatively engageable with the biopsy instrument for selective orientation of the tissue basket; and an optical sensor disposed adjacent a portion of the tubular knife member and being orientated to detect orientation of a lateral opening formed through the tubular knife member.

16. A biopsy system as recited in claim 15, wherein the first tubular member includes a first cam member configured and dimensioned to cooperate with indexing assembly to facilitate selective orientation of the tissue basket.

17. A biopsy system as recited in claim 16, the first cam member being configured to cooperate with a second cam member being disposed within the housing to orient the tissue basket to a predetermined orientation for obtaining a discrete tissue sample.

18. A biopsy system as recited in claim 16, the first cam member being configured to cooperate with a third cam member being disposed within the housing to orient the tissue basket to a predetermined orientation for removal of a tissue sample from the tissue basket.

19. A biopsy system as recited in claim 15, wherein the indexing assembly includes a manual gearing assembly configured to selectively manipulably orient the tissue basket.

20. A biopsy system comprising:

a housing;

a biopsy instrument being removably disposed within the housing and including a first tubular member having a tissue basket disposed at a distal end thereof, the tissue basket being configured for retrieval of tissue, the biopsy instrument further including a tubular knife member coaxially disposed relative to said first tubular member and configured for orientation relative to the first tubular member to sever tissue, a first cam member being mounted to the first tubular member and configured to engage a second cam member disposed at a proximal end of the biopsy instrument unit for orientation of the tissue basket; and a carriage being slideably disposed within the housing and being configured to releasably retain at least a portion of the biopsy instrument within the housing.

* * * * *